United States Patent
Wang et al.

(10) Patent No.: US 11,944,614 B2
(45) Date of Patent: Apr. 2, 2024

(54) IMIDAZO[4,5-C]PYRIDINE COMPOUNDS AS LSD-1 INHIBITORS

(71) Applicant: THE REGENTS OF THE UNIVERSITY OF MICHIGAN, Ann Arbor, MI (US)

(72) Inventors: Shaomeng Wang, Superior Township, MI (US); Rohan Rej, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 702 days.

(21) Appl. No.: 17/052,626

(22) PCT Filed: May 13, 2019

(86) PCT No.: PCT/US2019/031948
§ 371 (c)(1),
(2) Date: Nov. 3, 2020

(87) PCT Pub. No.: WO2019/222069
PCT Pub. Date: Nov. 21, 2019

(65) Prior Publication Data
US 2021/0236474 A1    Aug. 5, 2021

Related U.S. Application Data

(60) Provisional application No. 62/671,532, filed on May 15, 2018.

(51) Int. Cl.
| | | |
|---|---|---|
| C07D 471/04 | (2006.01) |
| A61K 31/437 | (2006.01) |
| A61K 31/439 | (2006.01) |
| A61K 31/4545 | (2006.01) |
| A61K 31/538 | (2006.01) |
| A61K 31/55 | (2006.01) |
| C07D 519/00 | (2006.01) |

(52) U.S. Cl.
CPC ........ *A61K 31/4545* (2013.01); *A61K 31/437* (2013.01); *A61K 31/439* (2013.01); *A61K 31/538* (2013.01); *A61K 31/55* (2013.01); *C07D 471/04* (2013.01); *C07D 519/00* (2013.01)

(58) Field of Classification Search
CPC .. C07D 487/04; C07D 471/04; C07D 519/00; A61K 31/437
See application file for complete search history.

(56) References Cited

U.S. PATENT DOCUMENTS

| | | | | |
|---|---|---|---|---|
| 11,168,082 B2 * | 11/2021 | Wang | ................... | C07D 471/04 |
| 2015/0225375 A1 | 8/2015 | Wu et al. | | |
| 2015/0225379 A1 | 8/2015 | Wu et al. | | |
| 2015/0225394 A1 | 8/2015 | Wu et al. | | |
| 2015/0225401 A1 | 8/2015 | Wu et al. | | |
| 2016/0009711 A1 | 1/2016 | Wu et al. | | |
| 2016/0009712 A1 | 1/2016 | Wu et al. | | |
| 2016/0009720 A1 | 1/2016 | Wu et al. | | |
| 2016/0009721 A1 | 1/2016 | Wu et al. | | |

FOREIGN PATENT DOCUMENTS

| | | |
|---|---|---|
| WO | WO-2016/007727 A1 | 1/2016 |
| WO | WO-2016/007736 A1 | 1/2016 |
| WO | WO-2016/161282 A1 | 10/2016 |
| WO | WO-2018/213211 A1 | 11/2018 |

OTHER PUBLICATIONS

Dreher et al., Lysine specific demethylase 1 is a molecular driver and therapeutic target in sarcoma, Frontiers in Oncology, pp. 1-16, published: Jan. 4, 2023.*
Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Simone, Introduction, Omenn, Cancer Prevention, Part XIV. Oncology, Cecil Textbook of Medicine, 20th Edition, vol. 1, pp. 1004-1010 (1996).*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Razonable et al., PubMed Abstract (Herpes 10(3):60-5), 2003.*
Merck Manual Professional Online Edition, Acute Leukemia, 6 pages, 2013.*
Bennani-Baiti et al., Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma, Hum. Pathol., 43(8):1300-7 (Aug. 2012).
Crea et al., The emerging role of histone lysine demethylases in prostate cancer, Mol. Cancer, 11:52 (Aug. 2012).
Ding et al., LSD1-mediated epigenetic modification contributes to proliferation and metastasis of colon cancer, Br. J. Cancer, 109(4):994-1003 (Aug. 2013).
Hayami et al., Overexpression of LSD1 contributes to human carcinogenesis through chromatin regulation in various cancers, Int. J. cancer, 128(3):574-86 (Feb. 2011).
International Application No. PCT/US2019/031948, International Search Report and Written Opinion, dated Jul. 19, 2019.

(Continued)

*Primary Examiner* — Deepak R Rao
(74) *Attorney, Agent, or Firm* — MARSHALL, GERSTEIN & BORUN LLP

(57) ABSTRACT

The present disclosure provides compounds represented by Formula I: and the pharmaceutically acceptable salts and solvates thereof, wherein $R^1$, $R^2$, $R^3$, and $R^4$ are as defined as set forth in the specification. The present disclosure also provides compounds of Formula I for use to treat a condition or disorder responsive to LSD1 inhibition such as cancer.

12 Claims, No Drawings

(56) References Cited

OTHER PUBLICATIONS

Kong et al., Immunohistochemical expression of RBP2 and LSD1 in papillary thyroid carcinoma, Rom. J. Morphol. Embryol., 54(3):499-503 (2013).

Konovalov et al., Analysis of the levels of lysine-specific demethylase 1 (LSD1) mRNA in human ovarian tumors and the effects of chemical LSD1 inhibitors in ovarian cancer cell lines, J. Ovarian Res., 6(1):75 (Oct. 2013).

Lim et al., Lysine-specific demethylase 1 (LSD1) is highly expressed in ER-negative breast cancers and a biomarker predicting aggressive biology, Carcinogenesis, 31(3):512-20 (Mar. 2010).

Lv et al., Over-expression of LSD1 promotes proliferation, migration and invasion in non-small cell lung cancer, PLoS One, 7(4):e35065 (2012).

Sareddy et al., KDM1 is a novel therapeutic target for the treatment of gliomas, Oncotarget, 4(1):18-28 (Jan. 2013).

Schulte et al., Lysine-specific demethylase 1 is strongly expressed in poorly differentiated neuroblastoma: implications for therapy, Cancer Res., 69(5):2065-71 (Mar. 2009).

Serce et al., Elevated expression of LSD1 (Lysine-specific demethylase 1) during tumour progression from pre-invasive to invasive ductal carcinoma of the breast, BMC Clin. Pathol., 12:13 (Aug. 2012).

Suikki et al., Genetic alterations and changes in expression of histone demethylases in prostate cancer, Prostate, 70(8):889-98 (Jun. 2010).

Yu et al., High expression of lysine-specific demethylase 1 correlates with poor prognosis of patients with esophageal squamous cell carcinoma, Biochem. Biophys. Res. Commun., 437(2):192-8 (Jul. 2013).

\* cited by examiner

IMIDAZO[4,5-C]PYRIDINE COMPOUNDS AS LSD-1 INHIBITORS

CROSS-REFERENCE TO RELATED APPLICATIONS

This is the U.S. national phase of International Application No. PCT/US2019/031948, filed May 13, 2019, which claims the benefit of U.S. Provisional Application No. 62/671,532, filed May 15, 2018, incorporated herein by reference in its entirety.

BACKGROUND OF THE INVENTION

Field of the Invention

The present disclosure provides lysine specific demethylase-1 inhibitors and therapeutic methods of treating conditions and diseases, e.g., cancer, wherein inhibition of lysine specific demethylase-1 provides a benefit.

Background

Overexpression of lysine specific demethylase-1 (LSD-1 or LSD1) is observed bladder cancer, non-small cell lung cancer (NSCLC), breast cancer, ovary cancer, glioma, colorectal cancer, sarcoma, neuroblastoma, prostate cancer, esophageal squamous cell carcinoma, papillary thyroid carcinoma, and other cancers. Overexpression of LSD1 is also associated with clinically aggressive cancers such as recurrent prostate cancer, NSCLC, glioma, breast, colon cancer, ovary cancer, esophageal squamous cell carcinoma, and neuroblastoma. Knockdown of LSD1 expression or treatment with small molecular LSD1 inhibitors results in decreased cancer cell proliferation and/or induction of apoptosis. See, e.g., Hayami et al., *Int J Cancer* 128:574-86 (2011); Lv et al., *PLoS One* 7:e35065 (2012); Serce et al., *BMC Clin Pathol* 12:13 (2012); Lim et al., *Carcinogenesis* 31:512-20 (2010); Konovalov and Garcia-Bassets, *J Ovarian Res* 6:75 (2013); Sareddy et al., *Oncotarget* 4:18-28 (2013); Ding et al., *Br J Cancer* 109:994-1003 (2013); Bennani-Baiti et al., *Hum Pathol* 43:1300-7 (2012); Schulte et al., *Cancer Res* 69:2065-71 (2009); Crea et al., *Mol Cancer* 11:52 (2012); Suikki et al., *Prostate* 70:889-98 (2010); Yu et al., *Biochem Biophys Res Commun.* 437:192-8 (2013); and Kong et al., *Rom J Morphol Embryol.* 54:499-503 (2013).

LSD1 inhibitors are being developed for the treatment of cancer and other diseases. For example, small molecule inhibitors of LSD1 are disclosed in US Patent Appl. Publication Nos. 2015/0225394, 2015/0225375, 2015/0225401, 2015/0225379, 2016/0009720, 2016/0009711, 2016/0009712, and 2016/0009721. There is a need in the art for new LSD1-inhibiting molecules.

BRIEF SUMMARY OF THE INVENTION

In one aspect, the present disclosure provides compounds represented by any one of Formulae I-VIII, below, and the pharmaceutically acceptable salts and solvates, e.g., hydrates, thereof, collectively referred to as "Compounds of the Disclosure." Compounds of the Disclosure are LSD1 inhibitors and/or synthetic intermediates used to make LSD1 inhibitors. LSD1 inhibitors are useful in treating or preventing diseases or conditions such as cancer wherein LSD1 inhibition provides a benefit.

In another aspect, the present disclosure provides methods of treating or preventing a condition or disease by administering a therapeutically effective amount of a Compound of the Disclosure to a subject, e.g., a human patient, in need thereof. The disease or condition of interest treatable or preventable by inhibition of LSD1 is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure may reduce the proliferation of unwanted cells by inducing apoptosis in those cells.

In another aspect, the present disclosure provides a method of inhibiting LSD1 in a subject, comprising administering to the subject a therapeutically effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of LSD1 provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Compounds of the Disclosure are LSD1 inhibitors.

In one embodiment, Compounds of the Disclosure are compounds represented by Formula I:

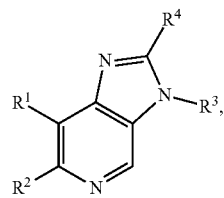

I or a pharmaceutically acceptable salt or solvate thereof, wherein:
- $R^1$ is selected from the group consisting of optionally substituted $C_6$-$C_{14}$ aryl and optionally substituted 5- to 14-membered heteroaryl;
- $R^2$ is selected from the group consisting of optionally substituted $C_6$-$C_{14}$ aryl and optionally substituted 5- to 14-membered heteroaryl;
- $R^3$ is selected from the group consisting of optionally substituted $C_{1-6}$ alkyl, (amino)alkyl, (heterocyclo)alkyl, (cycloalkyl)alkyl, and —C(=O)$R^{3a}$;
- $R^{3a}$ is optionally substituted heterocyclo; and
- $R^4$ is selected from the group consisting of hydrogen and $C_{1-6}$ alkyl.

In another embodiment, Compounds of the Disclosure are compounds represented by Formula I, or a pharmaceutically acceptable salt or solvate thereof, wherein the compound having Formula I is not (R)-2-fluoro-4-(6-(1-methyl-H-indazol-5-yl)-3-(pyrrolidin-3-ylmethyl)-3H-imidazo[4,5-c]pyridin-7-yl)benzonitrile.

In another embodiment, Compounds of the Disclosure are compounds represented by Formula I, or a pharmaceutically acceptable salt or solvate thereof, wherein $R^1$ is optionally substituted $C_6$-$C_{14}$ aryl. In another embodiment, $R^1$ is optionally substituted phenyl.

In another embodiment, Compounds of the Disclosure are compounds represented by Formula II:

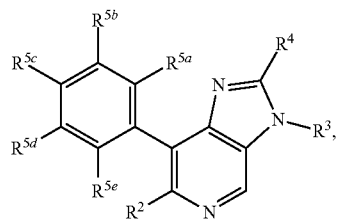

II or a pharmaceutically acceptable salt or solvate thereof, wherein:
- $R^{5a}$, $R^{5b}$, $R^{5c}$, $R^{5d}$, and $R^{5e}$ are each independently selected from the group consisting of hydrogen, halo, cyano, amino, hydroxy, $C_{1-4}$ alkyl, $C_{1-4}$ haloalkyl, and $C_{1-4}$ alkoxy; and
- $R^2$, $R^3$, and $R^4$ are as defined in connection with Formula I.

In another embodiment, Compounds of the Disclosure are compounds represented by Formula II, or a pharmaceutically acceptable salt or solvate thereof, wherein $R^{5c}$ is cyano.

In another embodiment, Compounds of the Disclosure are compounds represented by Formula II, or a pharmaceutically acceptable salt or solvate thereof, wherein $R^{5a}$ is hydrogen and $R^{5b}$ is selected from the group consisting of hydrogen and halo. In another embodiment, $R^{5a}$ is hydrogen and $R^{5b}$ is fluoro.

In another embodiment, Compounds of the Disclosure are compounds represented by Formula II, or a pharmaceutically acceptable salt or solvate thereof, where $R^{5d}$ and $R^{5e}$ are each hydrogen.

In another embodiment, Compounds of the Disclosure are compounds represented by Formula I, or a pharmaceutically acceptable salt or solvate thereof, or Formula II, or a pharmaceutically acceptable salt or solvate thereof, wherein:

$R^2$ is:

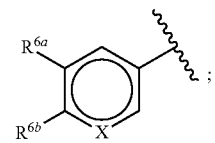

- $R^{6a}$ and $R^{6b}$ are independently selected from the group consisting of hydrogen, halo, cyano, amino, hydroxy, $C_{1-4}$ alkyl, $C_{1-4}$ haloalkyl, and $C_{1-4}$ alkoxy; or
- $R^{6a}$ and $R^{6b}$ taken together with the carbon atoms to which they are attached form a fused optionally substituted 5- or 6-membered heterocyclic group or optionally substituted 5- or 6-membered heteroaromatic group; and
- X is selected from the group consisting of —CH= and —N=.

In another embodiment, Compounds of the Disclosure are compounds represented by Formula I, or a pharmaceutically acceptable salt or solvate thereof, or Formula II, or a pharmaceutically acceptable salt or solvate thereof, wherein $R^2$ is selected from the group consisting of:

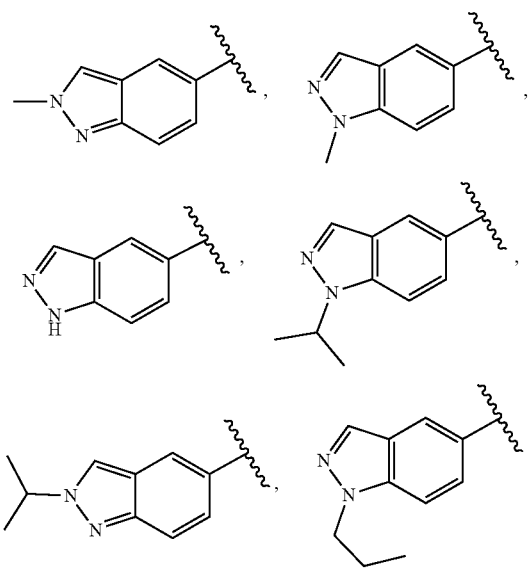

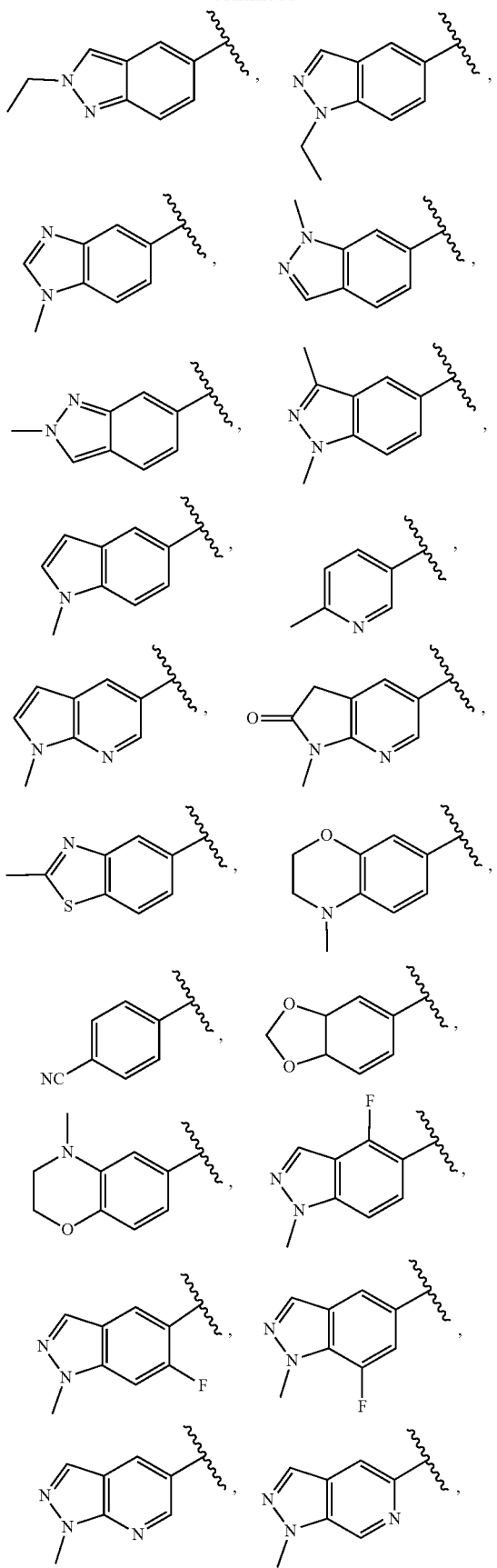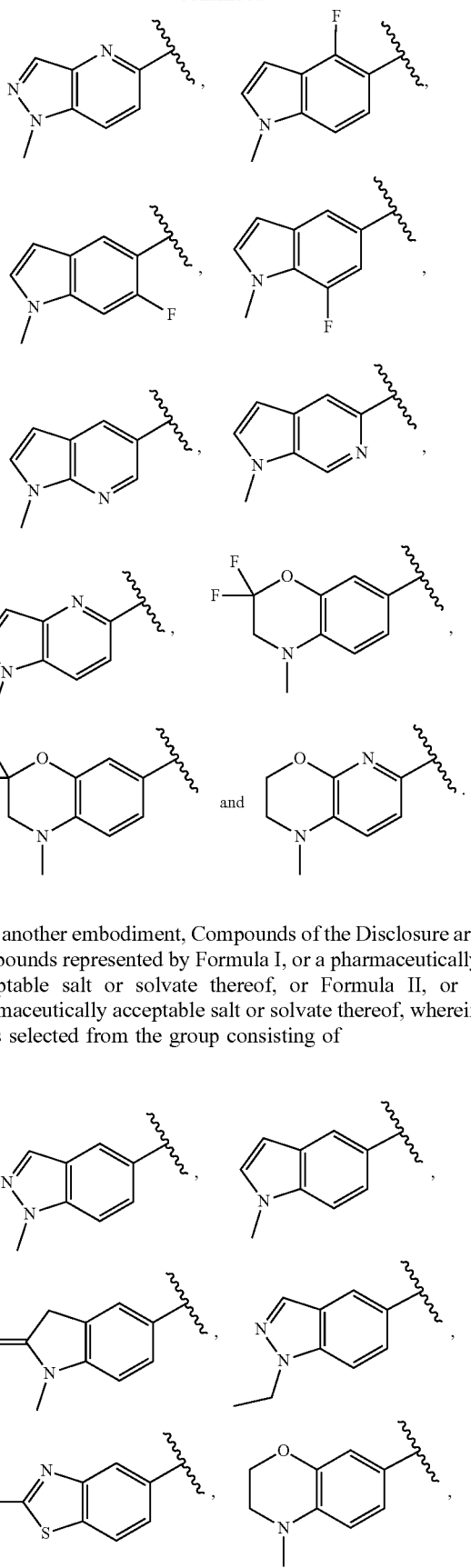
In another embodiment, Compounds of the Disclosure are compounds represented by Formula I, or a pharmaceutically acceptable salt or solvate thereof, or Formula II, or a pharmaceutically acceptable salt or solvate thereof, wherein $R^2$ is selected from the group consisting of -continued

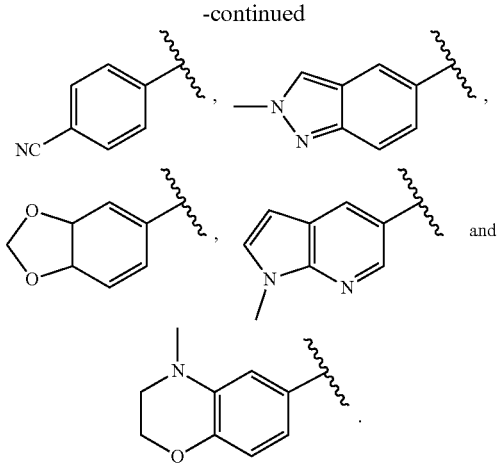

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is (heterocyclo)alkyl. In another embodiment, $R^3$ is (heterocyclo)-$CH_2$—.

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is selected from the group consisting of:

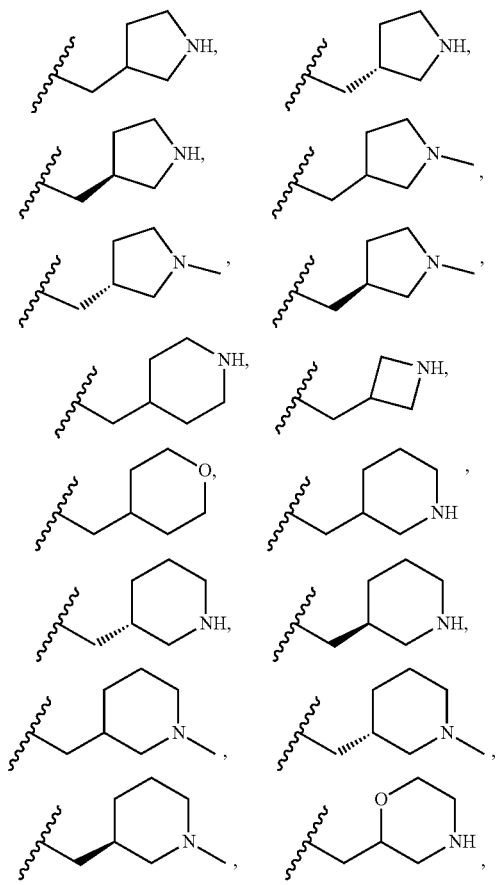

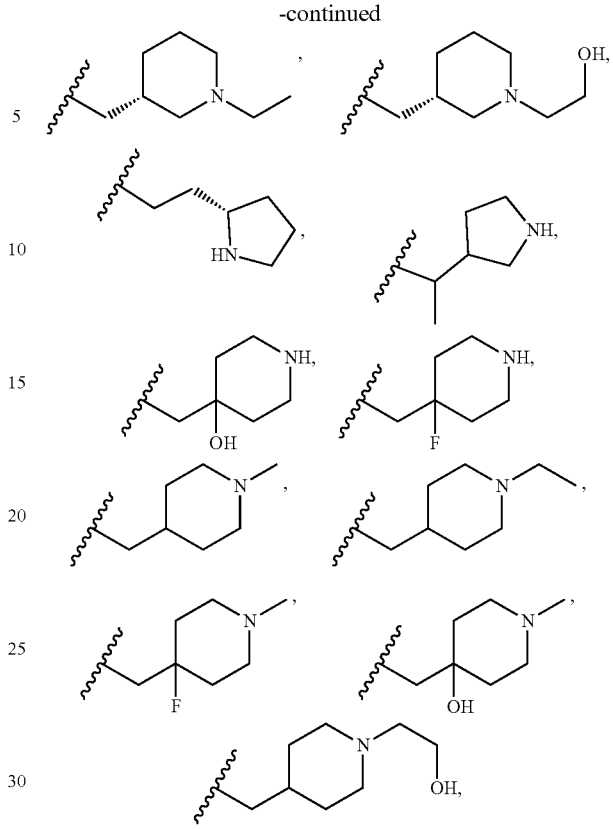

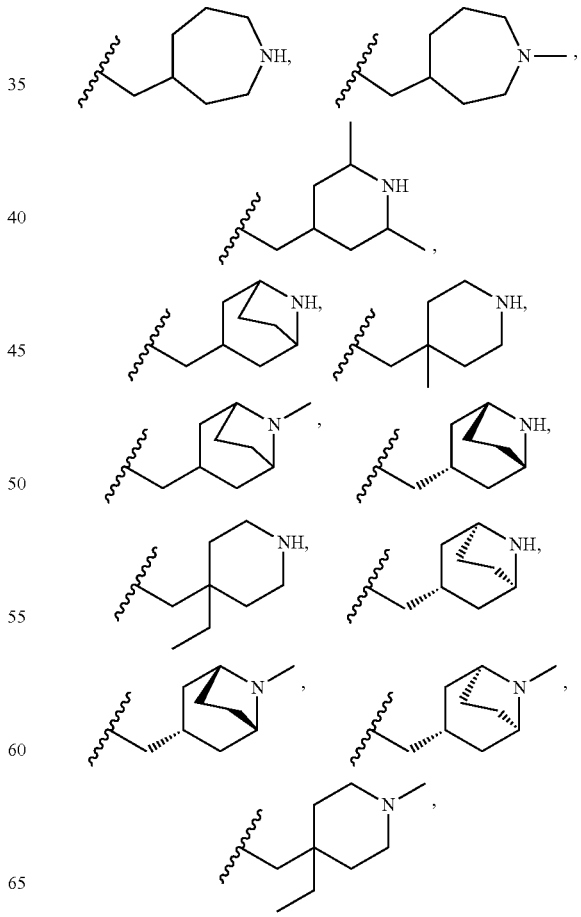

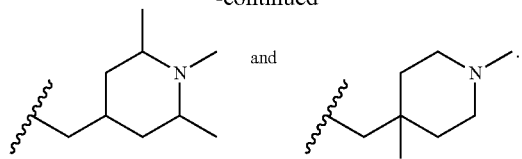

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is selected from the group consisting of:

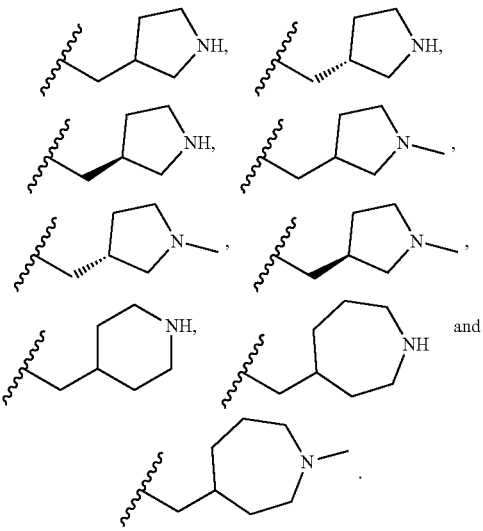

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is (cycloalkyl)alkyl. In another embodiment, $R^3$ is (cycloalkyl)-CH$_2$—. In another embodiment, $R^3$ is (amino-substituted cycloalkyl)-CH$_2$—. In another embodiment, $R^3$ is ((alkyl)amino-substituted cycloalkyl)-CH$_2$—.

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is selected from the group consisting of:

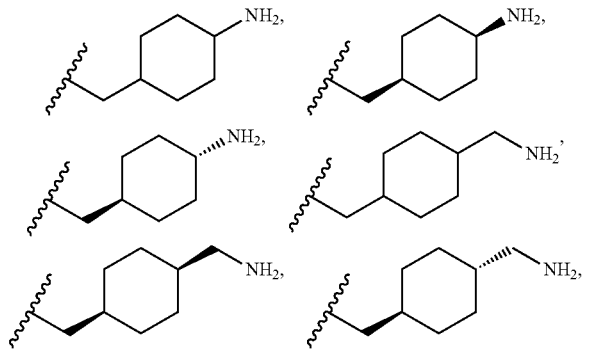

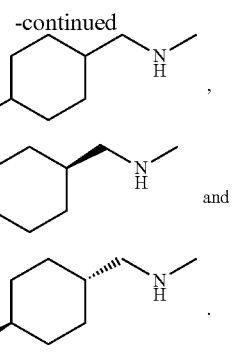

In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is (amino)alkyl, In another embodiment, Compounds of the Disclosure are compounds represented by Formula I, or a pharmaceutically acceptable salt or solvate thereof, or Formula II, or a pharmaceutically acceptable salt or solvate thereof, wherein $R^3$ is —C(=O)R$^{3a}$.

In another embodiment, Compounds of the Disclosure are compounds represented by Formula III:

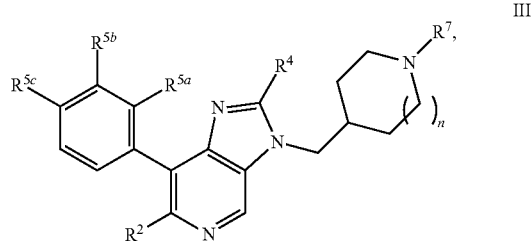

or a pharmaceutically acceptable salt or solvate thereof, wherein:
  $R^7$ is selected from the group consisting of hydrogen and $C_{1-4}$ alkyl;
  n is 0, 1, or 2;
  $R^2$ and $R^4$ are as defined in connection with Formula I; and
  $R^{5a}$, $R^{5b}$, and $R^{5c}$ are as defined in connection with Formula II.

In another embodiment, Compounds of the Disclosure are compounds represented by Formula IV:

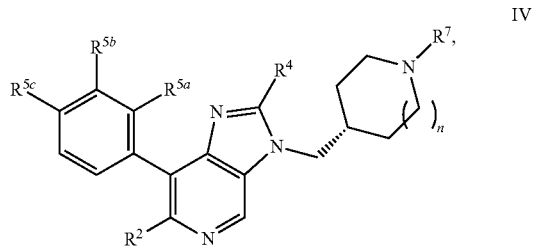

or a pharmaceutically acceptable salt or solvate thereof, wherein:

n is 0 or 2; and $R^2$, $R^4$, $R^{5a}$, $R^{5b}$, $R^{5c}$, and $R^7$ are as defined in connection with Formula III.

In another embodiment, Compounds of the Disclosure are compounds represented by Formula V:

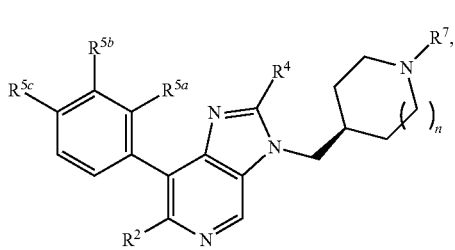

or a pharmaceutically acceptable salt or solvate thereof, wherein:

n is 0 or 2; and $R^2$, $R^4$, $R^{5a}$, $R^{5b}$, $R^{5c}$, and $R^7$ are as defined in connection with Formula III.

In another embodiment, Compounds of the Disclosure are compounds represented by Formula III, or a pharmaceutically acceptable salt or solvate thereof, wherein n is 1.

In another embodiment, Compounds of the Disclosure are compounds represented by any one of Formula III-V, or a pharmaceutically acceptable salt or solvate thereof, wherein n is 0.

In another embodiment, Compounds of the Disclosure are compounds represented by any one of Formula III-V, or a pharmaceutically acceptable salt or solvate thereof, wherein n is 2.

In another embodiment, Compounds of the Disclosure are compounds represented by any one of Formula III-V, or a pharmaceutically acceptable salt or solvate thereof, wherein $R^7$ is hydrogen.

In another embodiment, Compounds of the Disclosure are compounds represented by any one of Formula III-V, or a pharmaceutically acceptable salt or solvate thereof, wherein $R^7$ is $C_{1-4}$ alkyl. In another embodiment, $R^7$ is methyl.

In another embodiment, Compounds of the Disclosure are compounds represented by Formula VI:

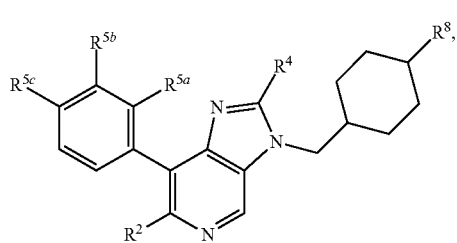

or a pharmaceutically acceptable salt or solvate thereof, wherein:

$R^8$ is selected from the group consisting of amino and (amino)alkyl;

$R^2$ and $R^4$ are as defined in connection with Formula I; and $R^{5a}$, $R^{5b}$, and $R^{5c}$ are as defined in connection with Formula II.

In another embodiment, Compounds of the Disclosure are compounds represented by Formula VII:

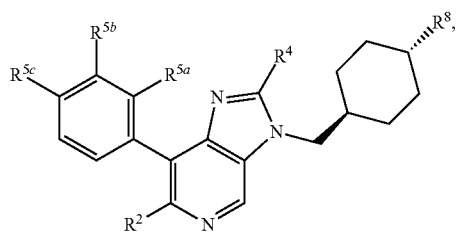

or a pharmaceutically acceptable salt or solvate thereof, wherein $R^2$, $R^4$, $R^{5a}$, $R^{5b}$, $R^{5c}$, and $R^8$ are as defined in connection with Formula VI.

In another embodiment, Compounds of the Disclosure are compounds represented by Formula VIII:

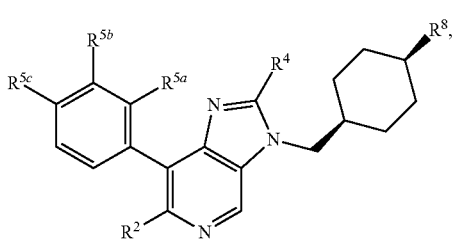

or a pharmaceutically acceptable salt or solvate thereof, wherein $R^2$, $R^4$, $R^{5a}$, $R^{5b}$, $R^{5c}$, and $R^8$ are as defined in connection with Formula VI.

In another embodiment, Compounds of the Disclosure are compounds represented by any one of Formulae I-VIII, or a pharmaceutically acceptable salt or solvate thereof, wherein $R^4$ is hydrogen.

In another embodiment, Compounds of the Disclosure are represented by any one or more of the compounds of Table 1, or a pharmaceutically acceptable salt or solvate thereof. In another embodiment, Compounds of the Disclosure are 2,2,2-trifluoroacetate (TFA) salts. In another embodiment, Compounds of the Disclosure are hydrochloric acid (HCl) salts.

TABLE 1

| Cpd. No. | Structure | Name |
|---|---|---|
| 1 | 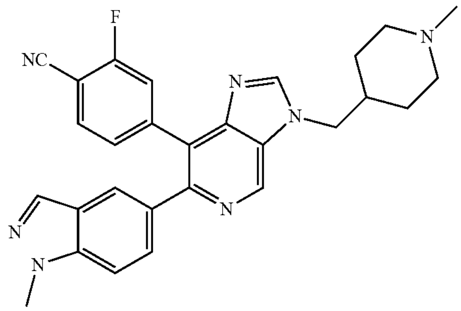 [SMILES: CNc1ccc(-c2ncc3c(ncn3CC3CCN(C)CC3)c2-c2ccc(C#N)c(F)c2)cc1C=N] | 2-fluoro-4-(6-(1-methyl-1H-indazol-5-yl)-3-((1-methylpiperidin-4-yl)methyl)-3H-imidazo[4,5-c]pyridin-7-yl)benzonitrile |
| 2 | 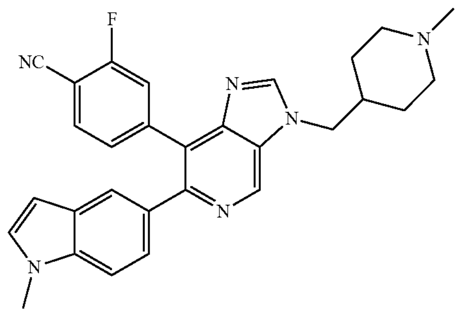 [SMILES: CN1CCC(Cn2cnc3c(-c4ccc(C#N)c(F)c4)c(-c4ccc5c(ccn5C)c4)ncc32)CC1] | 2-fluoro-4-(6-(1-methyl-1H-indol-5-yl)-3-((1-methylpiperidin-4-yl)methyl)-3H-imidazo[4,5-c]pyridin-7-yl)benzonitrile |
| 3 | 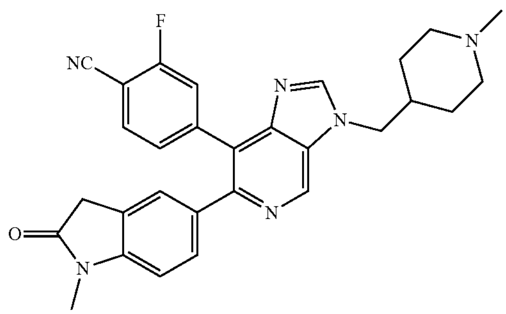 [SMILES: CN1CCC(Cn2cnc3c(-c4ccc(C#N)c(F)c4)c(-c4ccc5c(c4)CC(=O)N5C)ncc32)CC1] | 2-fluoro-4-(6-(1-methyl-2-oxoindolin-5-yl)-3-((1-methylpiperidin-4-yl)methyl)-3H-imidazo[4,5-c]pyridin-7-yl)benzonitrile |
| 4 | 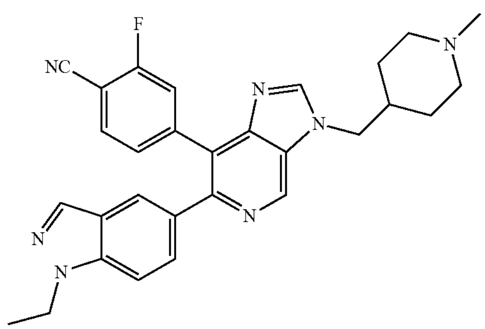 [SMILES: CCNc1ccc(-c2ncc3c(ncn3CC3CCN(C)CC3)c2-c2ccc(C#N)c(F)c2)cc1C=N] | 4-(6-(1-ethyl-1H-indazol-5-yl)-3-((1-methylpiperidin-4-yl)methyl)-3H-imidazo[4,5-c]pyridin-7-yl)-2-fluorobenzonitrile |
| 5 | 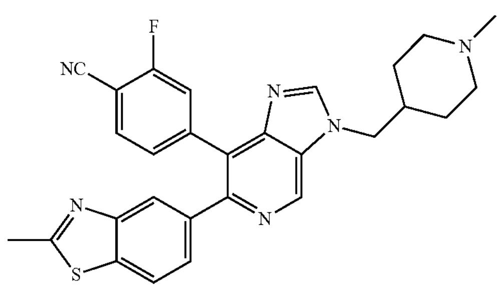 | 2-fluoro-4-(6-(2-methylbenzo[d]thiazol-5-yl)-3-((1-methylpiperidin-4-yl)methyl)-3H-imidazo[4,5-c]pyridin-7-yl)benzonitrile |

TABLE 1-continued

| Cpd. No. | Structure | Name |
|---|---|---|
| 6 | 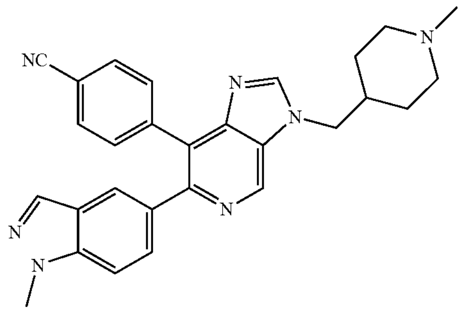 [SMILES: CNc1ccc(-c2ncc3c(ncn3CC3CCN(C)CC3)c2-c2ccc(C#N)cc2)cc1C=N] | 4-(6-(1-methyl-1H-indazol-5-yl)-3-((1-methylpiperidin-4-yl)methyl)-3H-imidazo[4,5-c]pyridin-7-yl)benzonitrile |
| 7 | 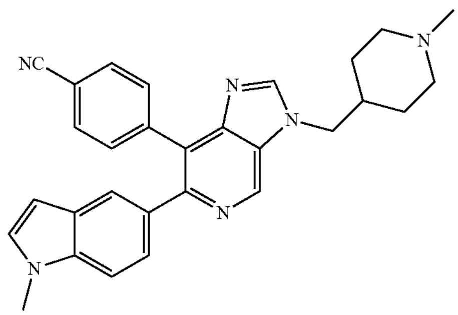 [SMILES: CN1CCC(Cn2cnc3c(-c4ccc(C#N)cc4)c(-c4ccc5c(ccn5C)c4)ncc32)CC1] | 4-(6-(1-methyl-1H-indol-5-yl)-3-((1-methylpiperidin-4-yl)methyl)-3H-imidazo[4,5-c]pyridin-7-yl)benzonitrile |
| 8 | 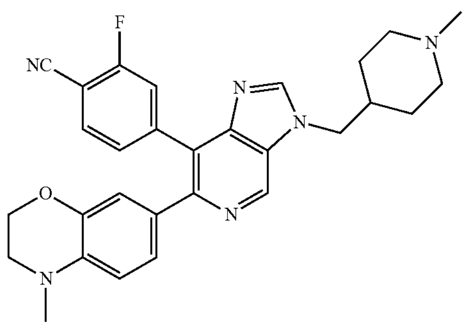 [SMILES: CN1CCC(Cn2cnc3c(-c4ccc(C#N)c(F)c4)c(-c4ccc5c(c4)OCCN5C)ncc32)CC1] | 2-fluoro-4-(6-(4-methyl-3,4-dihydro-2H-benzo[b][1,4]oxazin-7-yl)-3-((1-methylpiperidin-4-yl)methyl)-3H-imidazo[4,5-c]pyridin-7-yl)benzonitrile |
| 9 | 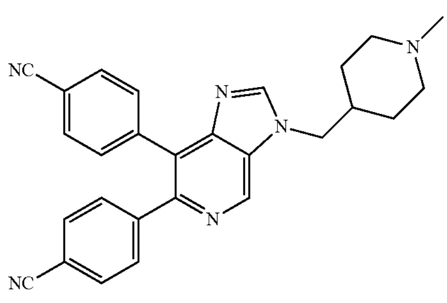 [SMILES: CN1CCC(Cn2cnc3c(-c4ccc(C#N)cc4)c(-c4ccc(C#N)cc4)ncc32)CC1] | 4,4'-(3-((1-methylpiperidin-4-yl)methyl)-3H-imidazo[4,5-c]pyridine-6,7-diyl)dibenzonitrile |
| 10 | 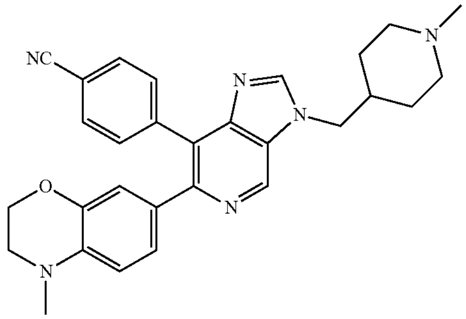 [SMILES: CN1CCC(Cn2cnc3c(-c4ccc(C#N)cc4)c(-c4ccc5c(c4)OCCN5C)ncc32)CC1] | 4-(6-(4-methyl-3,4-dihydro-2H-benzo[b][1,4]oxazin-7-yl)-3-((1-methylpiperidin-4-yl)methyl)-3H-imidazo[4,5-c]pyridin-7-yl)benzonitrile |

TABLE 1-continued

| Cpd. No. | Structure | Name |
|---|---|---|
| 11 | 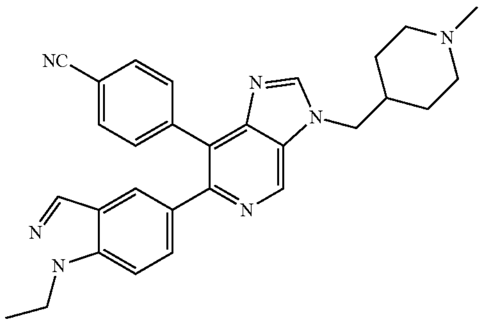 [SMILES: CCNc1ccc(-c2ncc3c(ncn3CC3CCN(C)CC3)c2-c2ccc(C#N)cc2)cc1C=N] | 4-(6-(1-ethyl-1H-indazol-5-yl)-3-((1-methylpiperidin-4-yl)methyl)-3H-imidazo[4,5-c]pyridin-7-yl)benzonitrile |
| 12 | 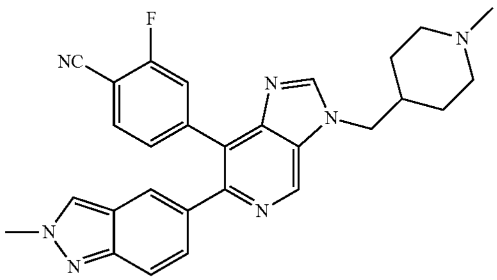 | 2-fluoro-4-(6-(2-methyl-2H-indazol-5-yl)-3-((1-methylpiperidin-4-yl)methyl)-3H-imidazo[4,5-c]pyridin-7-yl)benzonitrile |
| 13 | 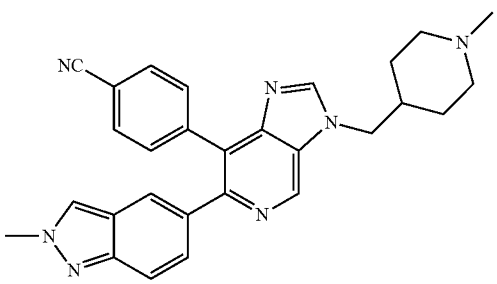 | 4-(6-(2-methyl-2H-indazol-5-yl)-3-((1-methylpiperidin-4-yl)methyl)-3H-imidazo[4,5-c]pyridin-7-yl)benzonitrile |
| 14 | 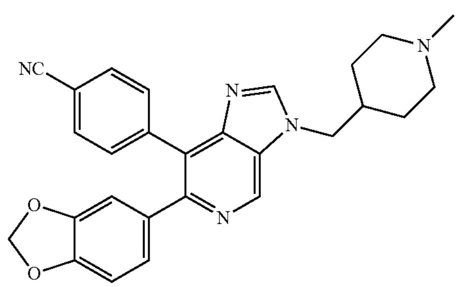 [SMILES: CN1CCC(Cn2cnc3c(-c4ccc(C#N)cc4)c(-c4ccc5c(c4)OCO5)ncc32)CC1] | 4-(6-(benzo[d][1,3]dioxol-5-yl)-3-((1-methylpiperidin-4-yl)methyl)-3H-imidazo[4,5-c]pyridin-7-yl)benzonitrile |
| 15 | 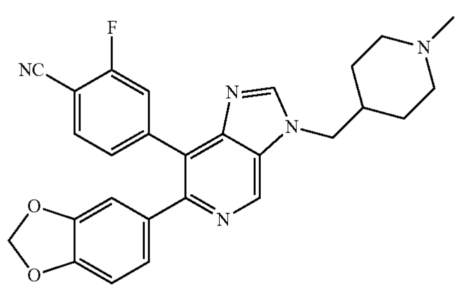 [SMILES: CN1CCC(Cn2cnc3c(-c4ccc(C#N)c(F)c4)c(-c4ccc5c(c4)OCO5)ncc32)CC1] | 4-(6-(benzo[d][1,3]dioxol-5-yl)-3-((1-methylpiperidin-4-yl)methyl)-3H-imidazo[4,5-c]pyridin-7-yl)-2-fluorobenzonitrile |

TABLE 1-continued

| Cpd. No. | Structure | Name |
|---|---|---|
| 16 | 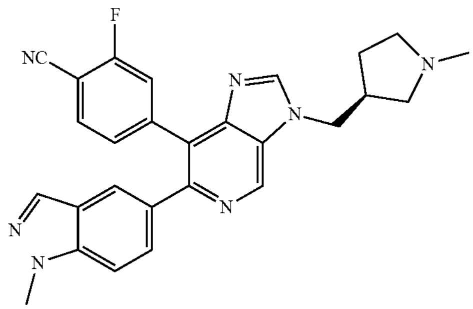 [SMILES: CNc1ccc(-c2ncc3c(ncn3C[C@H]3CCN(C)C3)c2-c2ccc(C#N)c(F)c2)cc1C=N] | (S)-2-fluoro-4-(6-(1-methyl-1H-indazol-5-yl)-3-((1-methylpyrrolidin-3-yl)methyl)-3H-imidazo[4,5-c]pyridin-7-yl)benzonitrile |
| 17 | 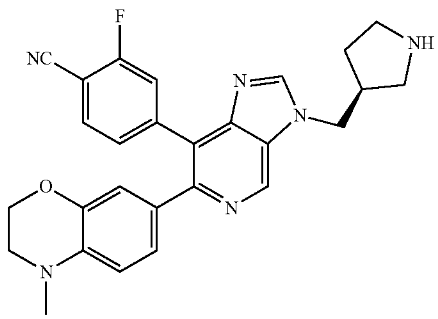 [SMILES: CN1CCOc2cc(-c3ncc4c(ncn4C[C@H]4CCNC4)c3-c3ccc(C#N)c(F)c3)ccc21] | (S)-2-fluoro-4-(6-(4-methyl-3,4-dihydro-2H-benzo[b][1,4]oxazin-7-yl)-3-(pyrrolidin-3-ylmethyl)-3H-imidazo[4,5-c]pyridin-7-yl)benzonitrile |
| 18 | 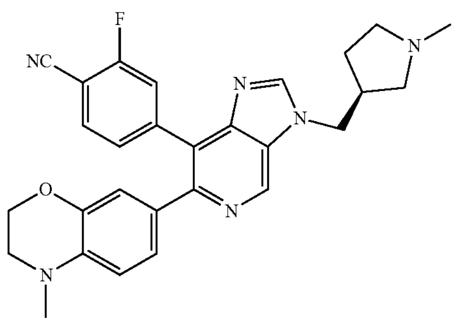 [SMILES: CN1CC[C@H](Cn2cnc3c(-c4ccc(C#N)c(F)c4)c(-c4ccc5c(c4)OCCN5C)ncc32)C1] | (S)-2-fluoro-4-(6-(4-methyl-3,4-dihydro-2H-benzo[b][1,4]oxazin-7-yl)-3-((1-methylpyrrolidin-3-yl)methyl)-3H-imidazo[4,5-c]pyridin-7-yl)benzonitrile |
| 19 | 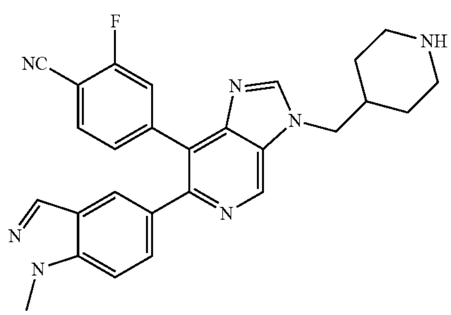 [SMILES: CNc1ccc(-c2ncc3c(ncn3CC3CCNCC3)c2-c2ccc(C#N)c(F)c2)cc1C=N] | 2-fluoro-4-(6-(1-methyl-1H-indazol-5-yl)-3-(piperidin-4-ylmethyl)-3H-imidazo[4,5-c]pyridin-7-yl)benzonitrile |
| 20 | 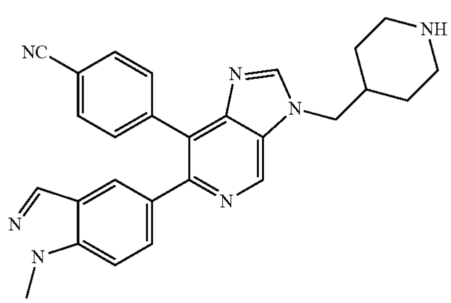 [SMILES: CNc1ccc(-c2ncc3c(ncn3CC3CCNCC3)c2-c2ccc(C#N)cc2)cc1C=N] | 4-(6-(1-methyl-1H-indazol-5-yl)-3-(piperidin-4-ylmethyl)-3H-imidazo[4,5-c]pyridin-7-yl)benzonitrile |

TABLE 1-continued

| Cpd. No. | Structure | Name |
|---|---|---|
| 21 | 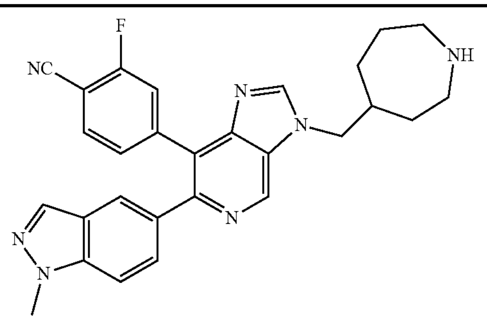 | 4-(3-(azepan-4-ylmethyl)-6-(1-methyl-1H-indazol-5-yl)-3H-imidazo[4,5-c]pyridin-7-yl)-2-fluorobenzonitrile |
| 22 | 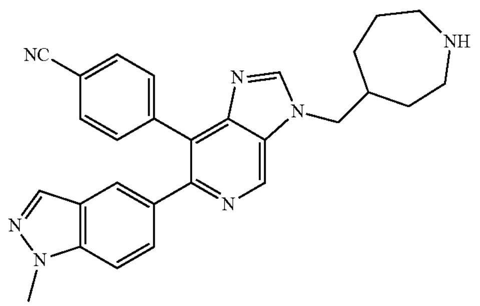 [SMILES: Cn1ncc2cc(-c3ncc4c(ncn4CC4CCCNCC4)c3-c3ccc(C#N)cc3)ccc21] | 4-(3-(azepan-4-ylmethyl)-6-(1-methyl-1H-indazol-5-yl)-3H-imidazo[4,5-c]pyridin-7-yl)benzonitrile |
| 23 | 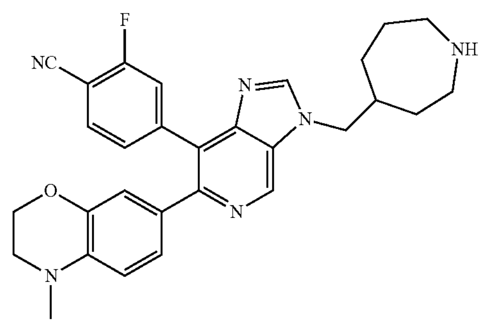 [SMILES: CN1CCOc2cc(-c3ncc4c(ncn4CC4CCCNCC4)c3-c3ccc(C#N)c(F)c3)ccc21] | 4-(3-(azepan-4-ylmethyl)-6-(4-methyl-3,4-dihydro-2H-benzo[b][1,4]oxazin-7-yl)-3H-imidazo[4,5-c]pyridin-7-yl)-2-fluorobenzonitrile |
| 24 | 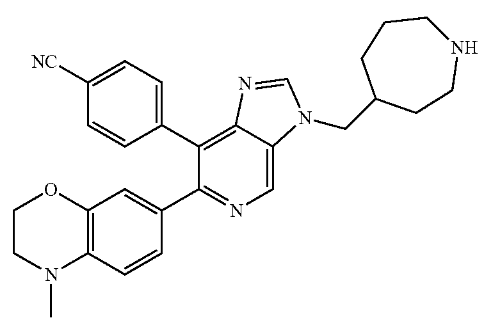 [SMILES: CN1CCOc2cc(-c3ncc4c(ncn4CC4CCCNCC4)c3-c3ccc(C#N)cc3)ccc21] | 4-(3-(azepan-4-ylmethyl)-6-(4-methyl-3,4-dihydro-2H-benzo[b][1,4]oxazin-7-yl)-3H-imidazo[4,5-c]pyridin-7-yl)benzonitrile |
| 25 | 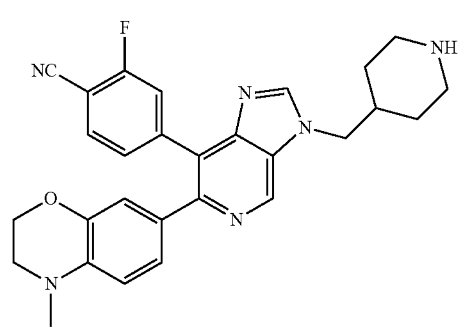 [SMILES: CN1CCOc2cc(-c3ncc4c(ncn4CC4CCNCC4)c3-c3ccc(C#N)c(F)c3)ccc21] | 2-fluoro-4-(6-(4-methyl-3,4-dihydro-2H-benzo[b][1,4]oxazin-7-yl)-3-(piperidin-4-ylmethyl)-3H-imidazo[4,5-c]pyridin-7-yl)benzonitrile |

TABLE 1-continued

| Cpd. No. | Structure | Name |
|---|---|---|
| 26 | 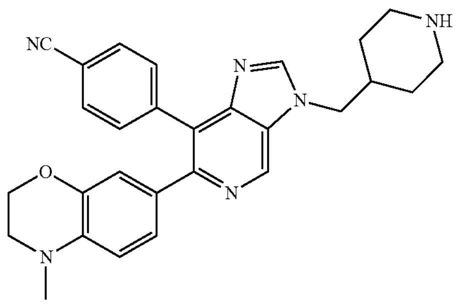 [SMILES: CN1CCOc2cc(-c3ncc4c(ncn4CC4CCNCC4)c3-c3ccc(C#N)cc3)ccc21] | 4-(6-(4-methyl-3,4-dihydro-2H-benzo[b][1,4]oxazin-7-yl)-3-(piperidin-4-ylmethyl)-3H-imidazo[4,5-c]pyridin-7-yl)benzonitrile |
| 27 | 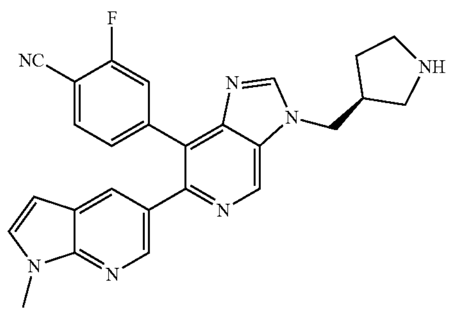 [SMILES: Cn1ccc2cc(-c3ncc4c(ncn4C[C@H]4CCNC4)c3-c3ccc(C#N)c(F)c3)cnc21] | (S)-2-fluoro-4-(6-(1-methyl-1H-pyrrolo[2,3-b]pyridin-5-yl)-3-(pyrrolidin-3-ylmethyl)-3H-imidazo[4,5-c]pyridin-7-yl)benzonitrile |
| 28 | 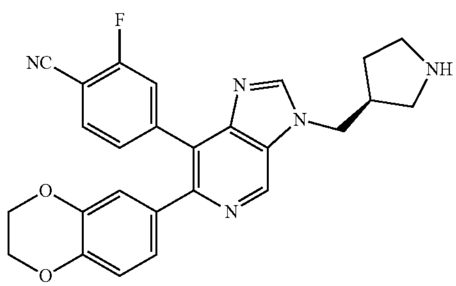 [SMILES: N#Cc1ccc(-c2c(-c3ccc4c(c3)OCCO4)ncc3c2ncn3C[C@H]2CCNC2)cc1F] | (S)-4-(6-(2,3-dihydrobenzo[b][1,4]dioxin-6-yl)-3-(pyrrolidin-3-ylmethyl)-3H-imidazo[4,5-c]pyridin-7-yl)-2-fluorobenzonitrile |
| 29 | 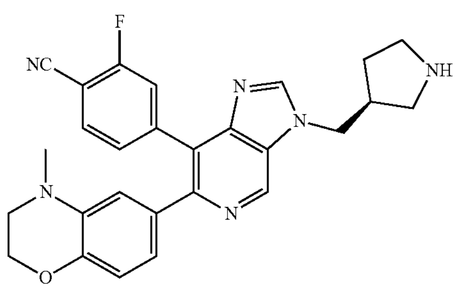 [SMILES: CN1CCOc2ccc(-c3ncc4c(ncn4C[C@H]4CCNC4)c3-c3ccc(C#N)c(F)c3)cc21] | (S)-2-fluoro-4-(6-(4-methyl-3,4-dihydro-2H-benzo[b][1,4]oxazin-6-yl)-3-(pyrrolidin-3-ylmethyl)-3H-imidazo[4,5-c]pyridin-7-yl)benzonitrile |
| 30 | 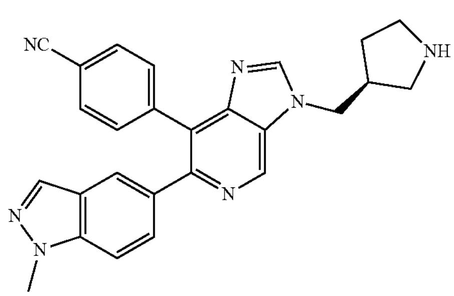 [SMILES: Cn1ncc2cc(-c3ncc4c(ncn4C[C@H]4CCNC4)c3-c3ccc(C#N)cc3)ccc21] | (S)-4-(6-(1-methyl-1H-indazol-5-yl)-3-(pyrrolidin-3-ylmethyl)-3H-imidazo[4,5-c]pyridin-7-yl)benzonitrile |

TABLE 1-continued

| Cpd. No. | Structure | Name |
|---|---|---|
| 31 | 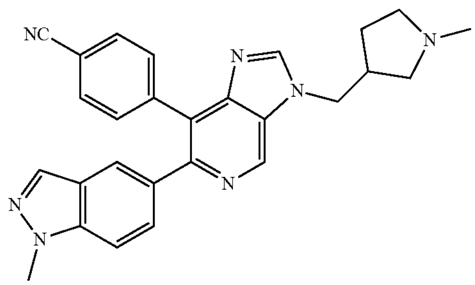 [SMILES: CN1CCC(Cn2cnc3c(-c4ccc(C#N)cc4)c(-c4ccc5c(cnn5C)c4)ncc32)C1] | 4-(6-(1-methyl-1H-indazol-5-yl)-3-((1-methylpyrrolidin-3-yl)methyl)-3H-imidazo[4,5-c]pyridin-7-yl)benzonitrile |
| 32 | 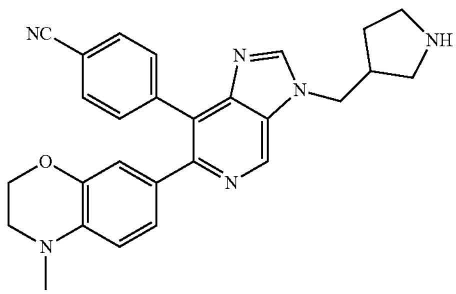 [SMILES: CN1CCOc2cc(-c3ncc4c(ncn4CC4CCNC4)c3-c3ccc(C#N)cc3)ccc21] | 4-(6-(4-methyl-3,4-dihydro-2H-benzo[b][1,4]oxazin-7-yl)-3-(pyrrolidin-3-ylmethyl)-3H-imidazo[4,5-c]pyridin-7-yl)benzonitrile |
| 33 | 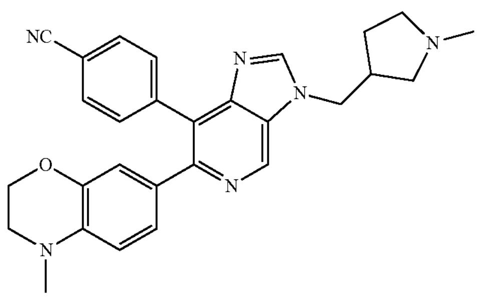 [SMILES: CN1CCC(Cn2cnc3c(-c4ccc(C#N)cc4)c(-c4ccc5c(c4)OCCN5C)ncc32)C1] | 4-(6-(4-methyl-3,4-dihydro-2H-benzo[b][1,4]oxazin-7-yl)-3-((1-methylpyrrolidin-3-yl)methyl)-3H-imidazo[4,5-c]pyridin-7-yl)benzonitrile |
| 34 | 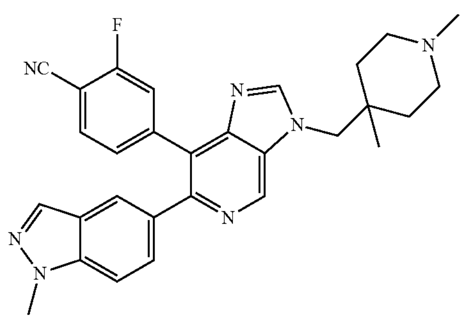 [SMILES: CN1CCC(C)(Cn2cnc3c(-c4ccc(C#N)c(F)c4)c(-c4ccc5c(cnn5C)c4)ncc32)CC1] | 4-(3-((1,4-dimethylpiperidin-4-yl)methyl)-6-(1-methyl-1H-indazol-5-yl)-3H-imidazo[4,5-c]pyridin-7-yl)-2-fluorobenzonitrile |
| 35 | 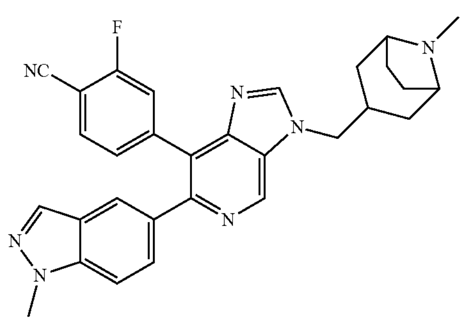 [SMILES: CN1C2CCC1CC(Cn1cnc3c(-c4ccc(C#N)c(F)c4)c(-c4ccc5c(cnn5C)c4)ncc31)C2] | 2-fluoro-4-(6-(1-methyl-1H-indazol-5-yl)-3-((8-methyl-8-azabicyclo[3.2.1]octan-3-yl)methyl)-3H-imidazo[4,5-c]pyridin-7-yl)benzonitrile |

TABLE 1-continued

| Cpd. No. | Structure | Name |
|---|---|---|
| 36 | 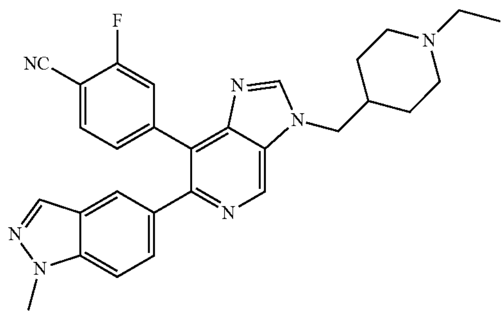 [SMILES: CCN1CCC(Cn2cnc3c(-c4ccc(C#N)c(F)c4)c(-c4ccc5c(cnn5C)c4)ncc32)CC1] | 4-(3-((1-ethylpiperidin-4-yl)methyl)-6-(1-methyl-1H-indazol-5-yl)-3H-imidazo[4,5-c]pyridin-7-yl)-2-fluorobenzonitrile |
| 37 | 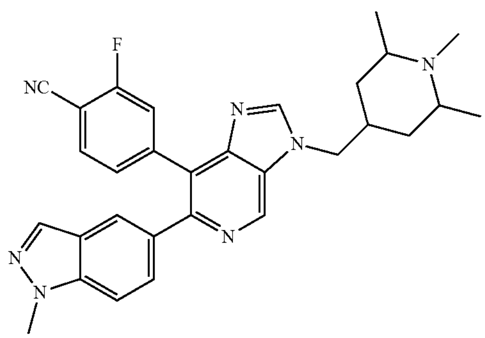 [SMILES: CC1CC(Cn2cnc3c(-c4ccc(C#N)c(F)c4)c(-c4ccc5c(cnn5C)c4)ncc32)CC(C)N1C] | 2-fluoro-4-(6-(1-methyl-1H-indazol-5-yl)-3-((1,2,6-trimethylpiperidin-4-yl)methyl)-3H-imidazo[4,5-c]pyridin-7-yl)benzonitrile |
| 38 | 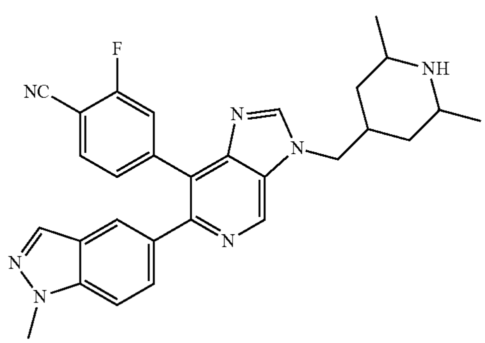 [SMILES: CC1CC(Cn2cnc3c(-c4ccc(C#N)c(F)c4)c(-c4ccc5c(cnn5C)c4)ncc32)CC(C)N1] | 4-(3-((2,6-dimethylpiperidin-4-yl)methyl)-6-(1-methyl-1H-indazol-5-yl)-3H-imidazo[4,5-c]pyridin-7-yl)-2-fluorobenzonitrile |
| 39 | 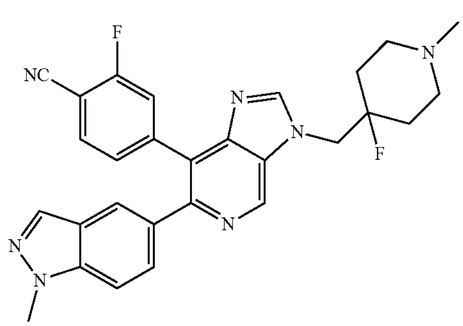 [SMILES: CN1CCC(F)(Cn2cnc3c(-c4ccc(C#N)c(F)c4)c(-c4ccc5c(cnn5C)c4)ncc32)CC1] | 2-fluoro-4-(3-((4-fluoro-1-methylpiperidin-4-yl)methyl)-6-(1-methyl-1H-indazol-5-yl)-3H-imidazo[4,5-c]pyridin-7-yl)benzonitrile |

TABLE 1-continued

| Cpd. No. | Structure | Name |
|---|---|---|
| 40 | 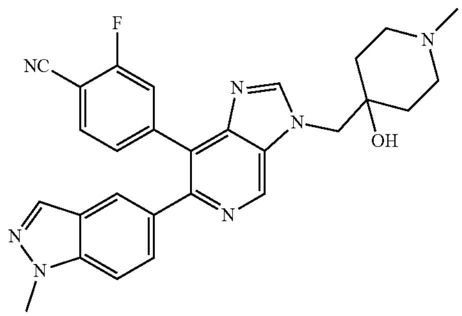 [SMILES: CN1CCC(O)(Cn2cnc3c(-c4ccc(C#N)c(F)c4)c(-c4ccc5c(cnn5C)c4)ncc32)CC1] | 2-fluoro-4-(3-((4-hydroxy-1-methylpiperidin-4-yl)methyl)-6-(1-methyl-1H-indazol-5-yl)-3H-imidazo[4,5-c]pyridin-7-yl)benzonitrile |
| 41 | 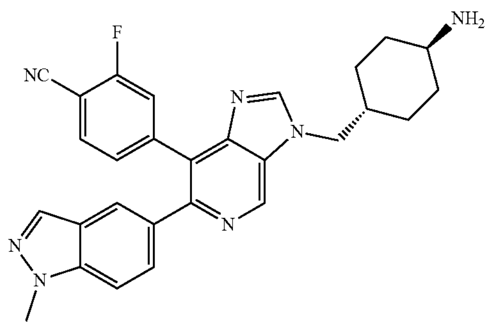 [SMILES: Cn1ncc2cc(-c3ncc4c(ncn4C[C@H]4CC[C@H](N)CC4)c3-c3ccc(C#N)c(F)c3)ccc21] | 4-(3-(((1r,4r)-4-aminocyclohexyl)methyl)-6-(1-methyl-1H-indazol-5-yl)-3H-imidazo[4,5-c]pyridin-7-yl)-2-fluorobenzonitrile |
| 42 | 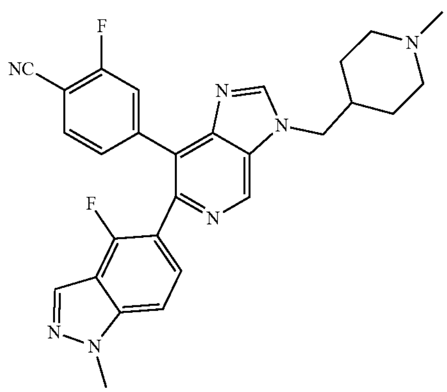 [SMILES: CN1CCC(Cn2cnc3c(-c4ccc(C#N)c(F)c4)c(-c4ccc5c(cnn5C)c4F)ncc32)CC1] | 2-fluoro-4-(6-(4-fluoro-1-methyl-1H-indazol-5-yl)-3-((1-methylpiperidin-4-yl)methyl)-3H-imidazo[4,5-c]pyridin-7-yl)benzonitrile |
| 43 | 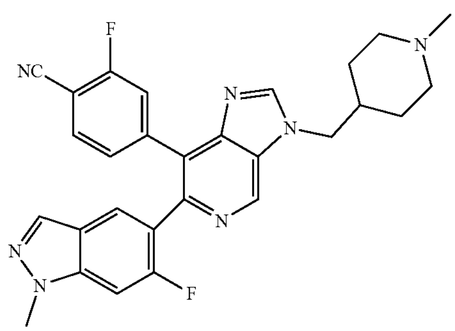 [SMILES: CN1CCC(Cn2cnc3c(-c4ccc(C#N)c(F)c4)c(-c4cc5cnn(C)c5cc4F)ncc32)CC1] | 2-fluoro-4-(6-(6-fluoro-1-methyl-1H-indazol-5-yl)-3-((1-methylpiperidin-4-yl)methyl)-3H-imidazo[4,5-c]pyridin-7-yl)benzonitrile |

TABLE 1-continued

| Cpd. No. | Structure | Name |
|---|---|---|
| 44 | 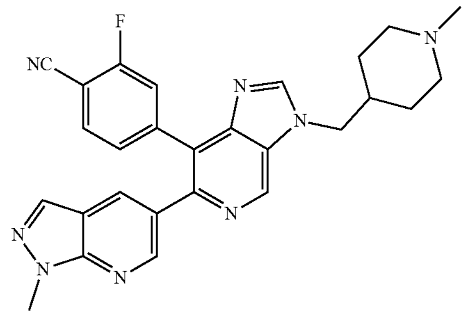 [SMILES: CN1CCC(Cn2cnc3c(-c4ccc(C#N)c(F)c4)c(-c4cnc5c(cnn5C)c4)ncc32)CC1] | 2-fluoro-4-(6-(1-methyl-1H-pyrazolo[3,4-b]pyridin-5-yl)-3-((1-methylpiperidin-4-yl)methyl)-3H-imidazo[4,5-c]pyridin-7-yl)benzonitrile |
| 45 | 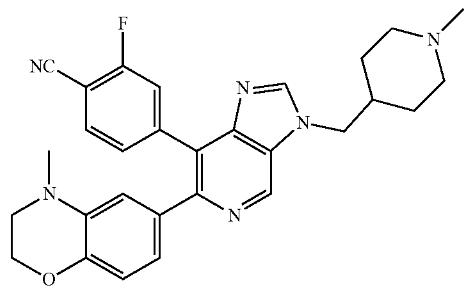 [SMILES: CN1CCC(Cn2cnc3c(-c4ccc(C#N)c(F)c4)c(-c4ccc5c(c4)N(C)CCO5)ncc32)CC1] | 2-fluoro-4-(6-(4-methyl-3,4-dihydro-2H-benzo[b][1,4]oxazin-6-yl)-3-((1-methylpiperidin-4-yl)methyl)-3H-imidazo[4,5-c]pyridin-7-yl)benzonitrile |
| 46 | 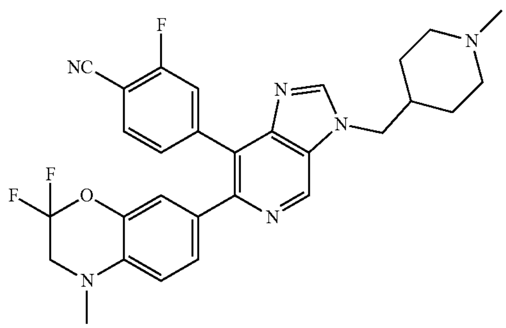 [SMILES: CN1CCC(Cn2cnc3c(-c4ccc(C#N)c(F)c4)c(-c4ccc5c(c4)OC(F)(F)CN5C)ncc32)CC1] | 4-(6-(2,2-difluoro-4-methyl-3,4-dihydro-2H-benzo[b][1,4]oxazin-7-yl)-3-((1-methylpiperidin-4-yl)methyl)-3H-imidazo[4,5-c]pyridin-7-yl)-2-fluorobenzonitrile |
| 47 | 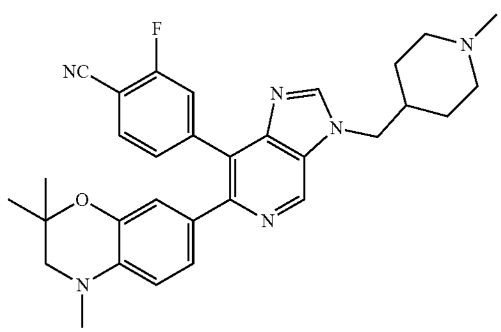 | 2-fluoro-4-(3-((1-methylpiperidin-4-yl)methyl)-6-(2,2,4-trimethyl-3,4-dihydro-2H-benzo[b][1,4]oxazin-7-yl)-3H-imidazo[4,5-c]pyridin-7-yl)benzonitrile |
| 48 | 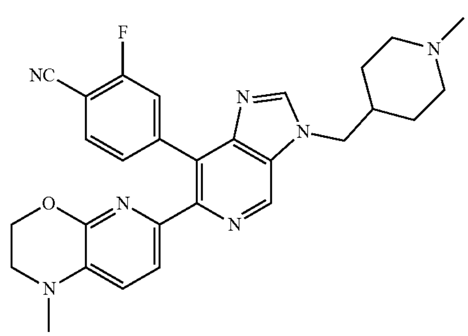 [SMILES: CN1CCC(Cn2cnc3c(-c4ccc(C#N)c(F)c4)c(-c4ccc5c(n4)OCCN5C)ncc32)CC1] | 2-fluoro-4-(6-(1-methyl-2,3-dihydro-1H-pyrido[2,3-b][1,4]oxazin-6-yl)-3-((1-methylpiperidin-4-yl)methyl)-3H-imidazo[4,5-c]pyridin-7-yl)benzonitrile |

TABLE 1-continued

| Cpd. No. | Structure | Name |
|---|---|---|
| 49 | 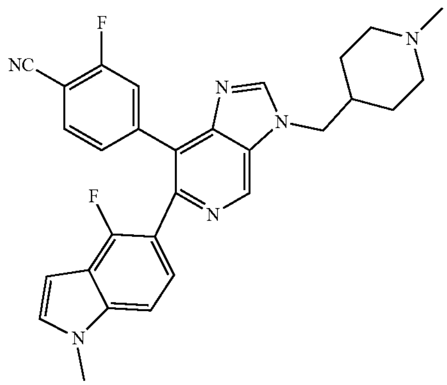 [SMILES: CN1CCC(Cn2cnc3c(-c4ccc(C#N)c(F)c4)c(-c4ccc5c(ccn5C)c4F)ncc32)CC1] | 2-fluoro-4-(6-(4-fluoro-1-methyl-1H-indol-5-yl)-3-((1-methylpiperidin-4-yl)methyl)-3H-imidazo[4,5-c]pyridin-7-yl)benzonitrile |
| 50 | 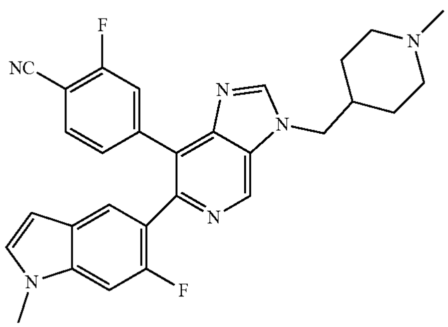 [SMILES: CN1CCC(Cn2cnc3c(-c4ccc(C#N)c(F)c4)c(-c4cc5ccn(C)c5cc4F)ncc32)CC1] | 2-fluoro-4-(6-(6-fluoro-1-methyl-1H-indol-5-yl)-3-((1-methylpiperidin-4-yl)methyl)-3H-imidazo[4,5-c]pyridin-7-yl)benzonitrile |
| 51 | 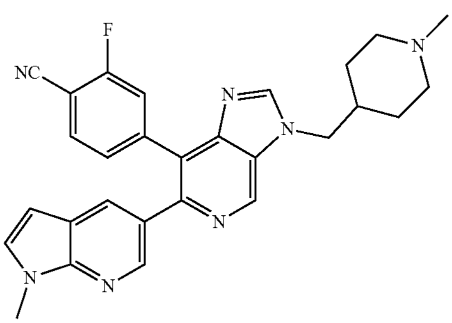 [SMILES: CN1CCC(Cn2cnc3c(-c4ccc(C#N)c(F)c4)c(-c4cnc5c(ccn5C)c4)ncc32)CC1] | 2-fluoro-4-(6-(1-methyl-1H-pyrrolo[2,3-b]pyridin-5-yl)-3-((1-methylpiperidin-4-yl)methyl)-3H-imidazo[4,5-c]pyridin-7-yl)benzonitrile |
| 52 | 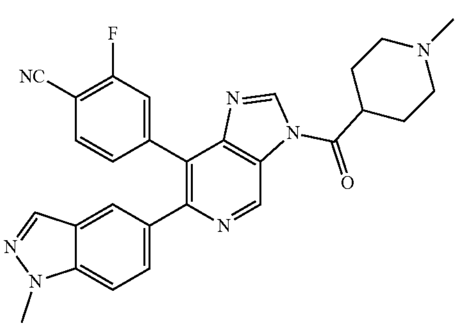 [SMILES: CN1CCC(C(=O)n2cnc3c(-c4ccc(C#N)c(F)c4)c(-c4ccc5c(cnn5C)c4)ncc32)CC1] | 2-fluoro-4-(6-(1-methyl-1H-indazol-5-yl)-3-(1-methylpiperidine-4-carbonyl)-3H-imidazo[4,5-c]pyridin-7-yl)benzonitrile |

TABLE 1-continued

| Cpd. No. | Structure | Name |
|---|---|---|
| 53 | 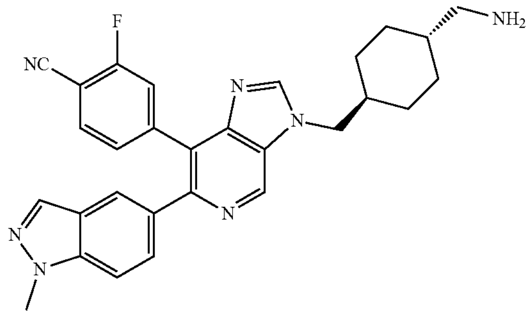 [SMILES: Cn1ncc2cc(-c3ncc4c(ncn4C[C@H]4CC[C@H](CN)CC4)c3-c3ccc(C#N)c(F)c3)ccc21] | 4-(3-(((1r,4r)-4-(aminomethyl)cyclohexyl)methyl)-6-(1-methyl-1H-indazol-5-yl)-3H-imidazo[4,5-c]pyridin-7-yl)-2-fluorobenzonitrile |
| 54 | 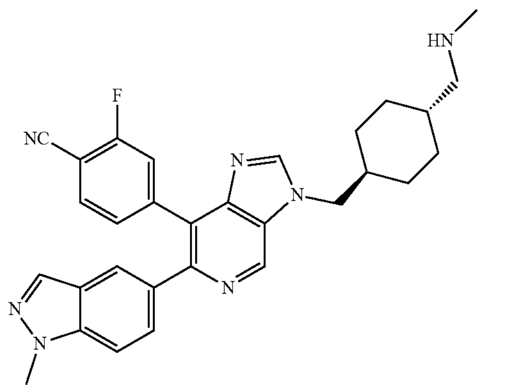 [SMILES: CNC[C@H]1CC[C@H](Cn2cnc3c(-c4ccc(C#N)c(F)c4)c(-c4ccc5c(cnn5C)c4)ncc32)CC1] | 2-fluoro-4-(6-(1-methyl-1H-indazol-5-yl)-3-(((1r,4r)-4-((methylamino)methyl)cyclohexyl)methyl)-3H-imidazo[4,5-c]pyridin-7-yl)benzonitrile |

Compounds of the Disclosure inhibit LSD1 and are useful in the treatment or prevention of a variety of diseases and conditions. In particular, Compounds of the Disclosure are useful in methods of treating or preventing a disease or condition wherein inhibition of LSD1 provides a benefit, for example, cancers and proliferative diseases. The therapeutic methods of this disclosure comprise administering a therapeutically effective amount of a Compound of the Disclosure to a subject in need thereof. The present methods also encompass administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

Certain of the Compounds of the Disclosure may exist as stereoisomers, i.e., isomers that differ only in the spatial arrangement of atoms, including optical isomers and conformational isomers (or conformers) and tautomers. The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" or "racemate" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry. Certain compounds of the Disclosure can have an ee of about 70% or more, e.g., about 80% or more, about 90% or more, about 91% or more, about 92% or more, about 93% or more, about 94% or more, about 95% or more, about 96% or more, about 97% or more, about 98% or more, or about 99% or more.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure. Certain compounds of the Disclosure are enantioenriched.

Salts and solvates, e.g., hydrates, of the Compounds of the Disclosure can also be used in the methods disclosed herein.

The present disclosure encompasses the preparation and use of salts of Compounds of the Disclosure. As used herein, a "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as inhibitors of LSD1 for the treatment of a variety of diseases and conditions, e.g., cancer, wherein LSD1 inhibition has a beneficial effect. Compounds of the Disclosure typically have a LSD1 inhibitory activity ($IC_{50}$) of less than 100 µM, e.g., less than about 50 M, less than about 25 M, and less than about 5 M, less than about 1 µM, less than about 0.5 µM, or less than about 0.1 µM In some embodiments, Compounds of the Disclosure have a LSD1 inhibitory activity ($IC_{50}$) of less than about 0.05 µM, less than about 0.01 µM, less than about 0.005 µM, or less than about 0.001 µM. In one embodiment, the present disclosure relates to a method of treating a subject suffering from a disease or condition wherein inhibition of LSD1 provides a benefit comprising administering a therapeutically effective amount of a Compound of the Disclosure to a subject in need thereof.

Since Compounds of the Disclosure are LSD1 inhibitors, a number of diseases and conditions mediated by LSD1 can be treated by employing these compounds. The present disclosure is thus directed generally to a method for treating a condition or disorder responsive to inhibition of LSD1, or an isoform or mutant thereof, in a subject, e.g., an animal, e.g., a human patient, suffering from, or at risk of suffering from, the condition or disorder, the method comprising administering to the subject an effective amount of one or more Compounds of the Disclosure. In one embodiment, the subject to be treated by the Compound of the Disclosure is a human cancer patient.

The present disclosure is also directed to a method of inhibiting LSD1, or an isoform or mutant thereof, in an animal, e.g., a human cancer patient, in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered.

Further provided are kits comprising a Compound of the Disclosure and, optionally, a second therapeutic agent useful in the treatment of diseases and conditions wherein inhibition of LSD1, or an isoform or mutant thereof, provides a benefit, packaged separately or together, and an insert having instructions for using these active agents.

In one embodiment, a Compound of the Disclosure is administered in conjunction with a second therapeutic agent useful in the treatment of a disease or condition, e.g., a disease or condition wherein inhibition of LSD1 or other therapeutic target provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to a subject in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, Diseases and conditions treatable by the methods of the present disclosure are cancer, a chronic autoimmune disorder, an inflammatory condition, or a proliferative disorder. In one embodiment, a human patient is treated with a Compound of the Disclosure, or a pharmaceutical composition comprising Compound of the Disclosure, wherein the compound is administered in an amount sufficient to inhibit LSD1 in the patient.

In one embodiment, the disease to be treated or prevented by the Compound of the Disclosure is cancer. In another embodiment, the present disclosure provides a method of treating or preventing cancer in subject in need thereof comprising administering a therapeutically effective amount of a Compound of the Disclosure to the subject. While not being limited to a specific mechanism, in some embodiments, Compounds of the Disclosure can treat or prevent cancer by inhibiting LSD1. Examples of treatable caners include, but are not limited to, any one or more of the cancers of Table 2.

TABLE 2 adrenal cancer
acinic cell carcinoma
acoustic neuroma
acral lentigious melanoma
acrospiroma
acute eosinophilic leukemia
acute erythroid leukemia
acute lymphoblastic leukemia
acute megakaryoblastic leukemia TABLE 2-continued acute monocytic leukemia
acute promyelocytic leukemia
adenocarcinoma
adenoid cystic carcinoma
adenoma
adenomatoid odontogenic tumor
adenosquamous carcinoma
adipose tissue neoplasm
adrenocortical carcinoma
adult T-cell leukemia/lymphoma
aggressive NK-cell leukemia
AIDS-related lymphoma
alveolar rhabdomyosarcoma
alveolar soft part sarcoma
ameloblastic fibroma
anaplastic large cell lymphoma
anaplastic thyroid cancer
angioimmunoblastic T-cell lymphoma,
angiomyolipoma
angiosarcoma
astrocytoma
atypical teratoid rhabdoid tumor
B-cell chronic lymphocytic leukemia
B-cell prolymphocytic leukemia
B-cell lymphoma
basal cell carcinoma
biliary tract cancer
bladder cancer
blastoma
bone cancer
Brenner tumor
Brown tumor
Burkitt's lymphoma
breast cancer
brain cancer
carcinoma
carcinoma in situ
carcinosarcoma
cartilage tumor
cementoma
myeloid sarcoma
chondroma
chordoma
choriocarcinoma
choroid plexus papilloma
clear-cell sarcoma of the kidney
craniopharyngioma
cutaneous T-cell lymphoma
cervical cancer
colorectal cancer
Degos disease
desmoplastic small round cell tumor
diffuse large B-cell lymphoma
dysembryoplastic neuroepithelial tumor,
dysgerminoma
embryonal carcinoma
endocrine gland neoplasm
endodermal sinus tumor
enteropathy-associated T-cell lymphoma
esophageal cancer
fetus in fetu
fibroma
fibrosarcoma
follicular lymphoma
follicular thyroid cancer
ganglioneuroma
gastrointestinal cancer
germ cell tumor
gestational choriocarcinoma
giant cell fibroblastoma
giant cell tumor of the bone
glial tumor
glioblastoma multiforme
glioma
gliomatosis cerebri
glucagonoma
gonadoblastoma
granulosa cell tumor
gynandroblastoma
gallbladder cancer

TABLE 2-continued gastric cancer
hairy cell leukemia
hemangioblastoma
head and neck cancer
hemangiopericytoma
hematological malignancy
hepatoblastoma
hepatosplenic T-cell lymphoma
Hodgkin's lymphoma
non-Hodgkin's lymphoma
invasive lobular carcinoma
intestinal cancer
kidney cancer
laryngeal cancer
lentigo maligna
lethal midline carcinoma
leukemia
leydig cell tumor
liposarcoma
lung cancer
lymphangioma
lymphangiosarcoma
lymphoepithelioma
lymphoma
acute lymphocytic leukemia
acute myelogeous leukemia
chronic lymphocytic leukemia
liver cancer
small cell lung cancer
non-small cell lung cancer
MALT lymphoma
malignant fibrous histiocytoma
malignant peripheral nerve sheath tumor
malignant triton tumor
mantle cell lymphoma
marginal zone B-cell lymphoma
mast cell leukemia
mediastinal germ cell tumor
medullary carcinoma of the breast
medullary thyroid cancer,
medulloblastoma
melanoma,
meningioma,
merkel cell cancer
mesothelioma
metastatic urothelial carcinoma
mixed Mullerian tumor
mucinous tumor
multiple myeloma
muscle tissue neoplasm
mycosis fungoides
myxoid liposarcoma
myxoma
myxosarcoma
nasopharyngeal carcinoma
neurinoma
neuroblastoma
neurofibroma
neuroma
nodular melanoma
ocular cancer
oligoastrocytoma
oligodendroglioma
oncocytoma
optic nerve sheath meningioma
optic nerve tumor
oral cancer
osteosarcoma
ovarian cancer
Pancoast tumor
papillary thyroid cancer
paraganglioma
pinealoblastoma
pineocytoma
pituicytoma
pituitary adenoma
pituitary tumor
plasmacytoma
polyembryoma
precursor T-lymphoblastic lymphoma

TABLE 2-continued primary central nervous system lymphoma
primary effusion lymphoma
preimary peritoneal cancer
prostate cancer
pancreatic cancer
pharyngeal cancer
pseudomyxoma periotonei
renal cell carcinoma
renal medullary carcinoma
retinoblastoma
rhabdomyoma
rhabdomyosarcoma
Richter's transformation
rectal cancer
sarcoma
Schwannomatosis
seminoma
Sertoli cell tumor
sex cord-gonadal stromal tumor
signet ring cell carcinoma
skin cancer
small blue round cell tumors
small cell carcinoma
soft tissue sarcoma
somatostatinoma
soot wart
spinal tumor
splenic marginal zone lymphoma
squamous cell carcinoma
synovial sarcoma
Sezary's disease
small intestine cancer
squamous carcinoma
stomach cancer
T-cell lymphoma
testicular cancer
thecoma
thyroid cancer
transitional cell carcinoma
throat cancer
urachal cancer
urogenital cancer
urothelial carcinoma
uveal melanoma
uterine cancer
verrucous carcinoma
visual pathway glioma
vulvar cancer
vaginal cancer
Waldenstrom's macroglobulinemia
Warthin's tumor
Wilms' tumor In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, or papillary thyroid carcinoma.

In another embodiment, the cancer is anaplastic large-cell lymphoma, non-small cell lung cancer, diffuse large B-cell lymphoma, inflammatory myofibroblastic tumors, neuroblastoma, anaplastic thyroid cancer, and rhabdomyosarcoma.

In another embodiment, the cancer is breast cancer, colorectal cancer, esophageal squamous cell cancer, and renal cell carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the LSD1 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Non-limiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Non-limiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; *vinca* alkaloids, such as vinblastine, vinblastine sulfate, vincristine, and vincristine sulfate, and vinorelbine; discodermolides; cochicine and epothilones and derivatives thereof.

Exemplary non-limiting alkylating agents include cyclophosphamide, ifosfamide, melphalan, and nitrosoureas, such as carmustine and lomustine.

Exemplary non-limiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary non-limiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary non-limiting mTOR inhibitors include compounds that inhibit the mammalian target of rapamycin (mTOR) and possess antiproliferative activity such as sirolimus, everolimus, CCI-779, and ABT578.

Exemplary non-limiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary non-limiting platin compounds include carboplatin, cis-platin, cisplatinum, and oxaliplatin.

Exemplary non-limiting methionine aminopeptidase inhibitors include bengamide or a derivative thereof and PPI-2458.

Exemplary non-limiting bisphosphonates include etridonic acid, clodronic acid, tiludronic acid, pamidronic acid, alendronic acid, ibandronic acid, risedronic acid, and zoledronic acid.

Exemplary non-limiting antiproliferative antibodies include trastuzumab, trastuzumab-DM, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary non-limiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary non-limiting telomerase inhibitors include compounds that target, decrease, or inhibit the activity of telomerase, such as compounds that inhibit the telomerase receptor, such as telomestatin.

Exemplary non-limiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary non-limiting Flt-3 inhibitors include PKC412, midostaurin, a staurosporine derivative, SU11248, and MLN518.

Exemplary non-limiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU1O1, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, non-limiting, exemplary chemotherapeutic compounds, one or more of which may be used in combination with a present LSD1 inhibitors include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present LSD1 inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure. In one embodiment, the disclosure provides a pharmaceutical composition comprising a Compound of the Disclosure and a pharmaceutically acceptable excipient.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, e.g., from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, e.g., about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A composition for intravenous, cutaneous, or subcutaneous injection typically contains an isotonic vehicle.

Compounds of the Disclosure can be readily combined with pharmaceutically acceptable carriers well-known in the art. In one embodiment, a pharmaceutical composition comprising a Compound of the Disclosure, or a pharmaceutically acceptable salt or hydrate thereof, and a pharmaceutically acceptable carrier, is provided. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "a disease or condition wherein inhibition of LSD1 provides a benefit" pertains to a disease or condition in which LSD1, is important or necessary, e.g., for the onset, progress, expression of that disease or condition, or a disease or a condition which is known to be treated by an LSD1 inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a LSD1 inhibitor for any particular cell type, for example, by assays which conveniently can be used to assess the activity of particular compounds.

The terms "LSD1," "lysine specific demethylase-1," "lysine-specific histone demethylase 1A," "lysine (K)-specific demethylase 1A," or "LSD-1" are synonymous terms that refer to a protein in humans encoded by the KDM1A gene. The term LSD1 includes isoforms and mutants of LSD1. LSD1 is a flavin-dependent monoamine oxidase, which can demethylate mono- and di-methylated lysines, specifically histone 3, lysines 4 and 9 (H3K4 and H3K9).

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of LSD1 and can be used in treating or preventing diseases and conditions wherein inhibition of LSD1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group means that the alkyl as defined above is either unsubstituted or substituted with one, two, or three substituents independently selected from the group consisting of nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and cycloalkyl. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$SO$_2$CH$_3$, CH$_2$CH$_2$CO$_2$H, —CH$_2$CH$_2$SO$_2$CH$_3$, —CH$_2$CH$_2$COPh, and —CH$_2$C$_6$H$_{11}$.

In the present disclosure, the term "cycloalkyl" as used by itself or as part of another group refers to saturated and partially unsaturated (containing one or two double bonds) cyclic aliphatic hydrocarbons containing one, two, or three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

In the present disclosure, the term "optionally substituted cycloalkyl" as used by itself or as part of another group means that the cycloalkyl as defined above is either unsubstituted or substituted with one, two, or three substituents independently selected from the group consisting of from halo, nitro, cyano, hydroxy, amino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent. In another embodiment, the optionally substituted cycloalkyl is substituted with one amino or (amino)alkyl substituent. Non-limiting exemplary optionally substituted cycloalkyl groups include:

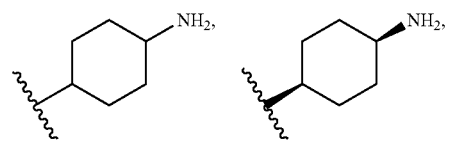

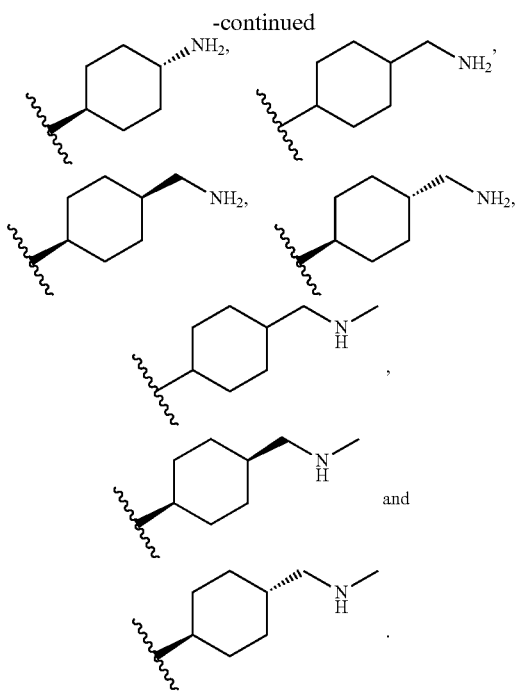

In the present disclosure, the term "alkenyl" as used by itself or as part of another group refers to an alkyl group as defined above containing one, two, or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "alkynyl" as used by itself or as part of another group refers to an alkyl group as defined above containing one, two, or three carbon-to-carbon triple bonds. In one embodiment, the alkynyl has one carbon-to-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is a $C_{1-4}$ alkoxy group. In another embodiment, the alkoxy group is a $C_{1-4}$ alkyl attached to a terminal oxygen atom, e.g., methoxy, ethoxy, and tert-butoxy.

In the present disclosure, the term "alkylthio" as used by itself or as part of another group refers to a sulfur atom substituted by an optionally substituted alkyl group. In one embodiment, the alkylthio group is a $C_{1-4}$ alkylthio group. Non-limiting exemplary alkylthio groups include —SCH$_3$ and —SCH$_2$CH$_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms, i.e., $C_6$-$C_{14}$ aryl, or the number of carbon atoms designated. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

In the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

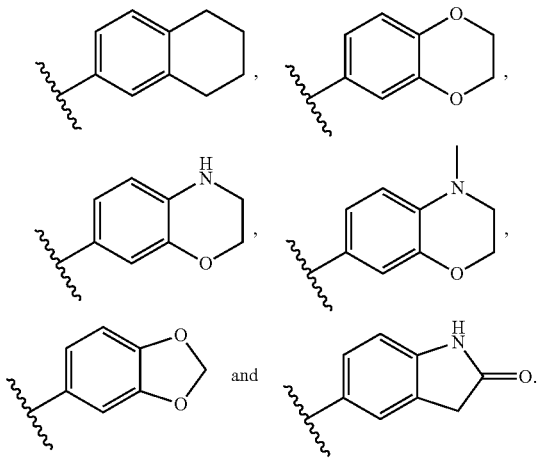

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is PhCH$_2$O—.

In the present disclosure, the term "heteroaryl" or "heteroaromatic" refers to monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" is also meant to include possible N-oxides. A non-limiting exemplary N-oxide is pyridyl N-oxide. The heteroaryl can be attached to the remained of the molecule through any available carbon or nitrogen atom.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted.

The term optionally substituted heteroaryl is also meant to include groups having fused optionally substituted cycloalkyl and fused optionally substituted heterocyclo rings. Non-limiting examples include:

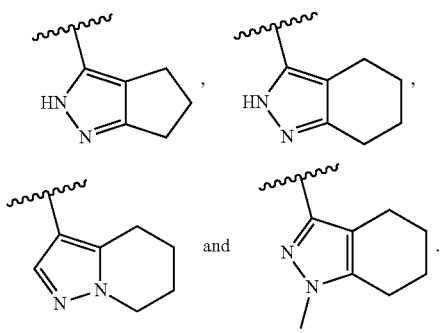

In another embodiment, the heteroaryl is an optionally substituted 9- to 14-membered bicyclic aromatic ring system, wherein at least one carbon atom of one of the rings is replaced with a heteroatom independently selected from the group consisting of oxygen, nitrogen, and sulfur. In another embodiment, the heteroaryl is an optionally substituted 9-membered bicyclic aromatic ring system, wherein one or two carbon atoms of one of the rings is replaced with a heteroatom independently selected from the group consisting of oxygen, nitrogen, and sulfur. Non-limiting exemplary 9- to 14-membered bicyclic aromatic ring systems include:

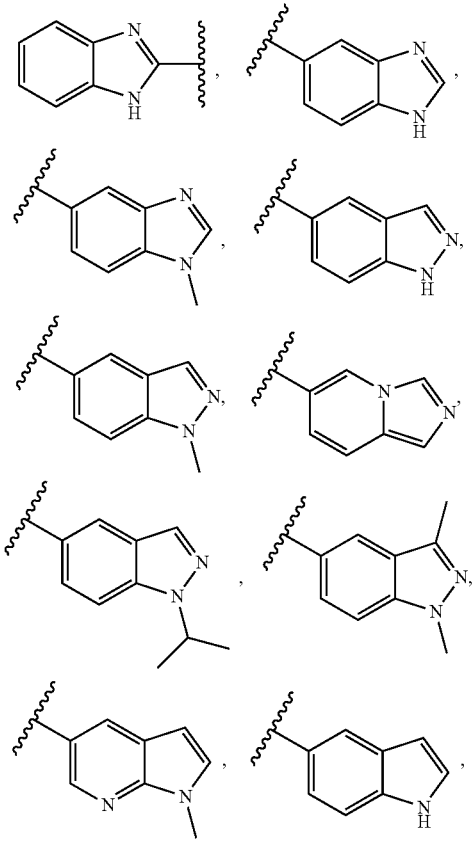

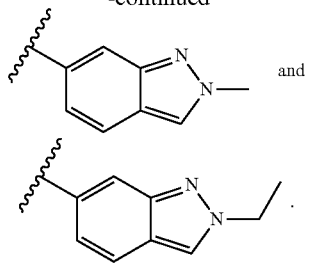

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members, i.e., a 3- to 14-membered heterocyclo, wherein at least one carbon atom of one of the rings is replaced with a heteroatom. In one embodiment, the heterocyclo is a 4- to 8-membered heterocyclo. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(═O)—, for example, cyclic ureido groups such as 2-imidazolidinone and cyclic amide groups such as β-lactam, γ-lactam, δ-lactam, F-lactam, and piperazin-2-one. The term "heterocyclo" is also meant to include groups having fused optionally substituted aryl groups, e.g., indolinyl, chroman-4-yl. In one embodiment, the heterocyclo group is a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, alkoxycarbonyl, CF$_3$C(═O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

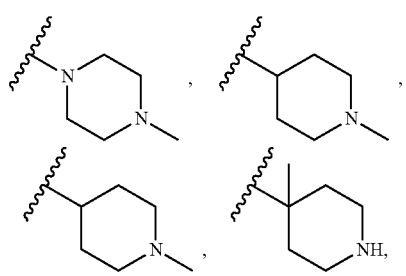

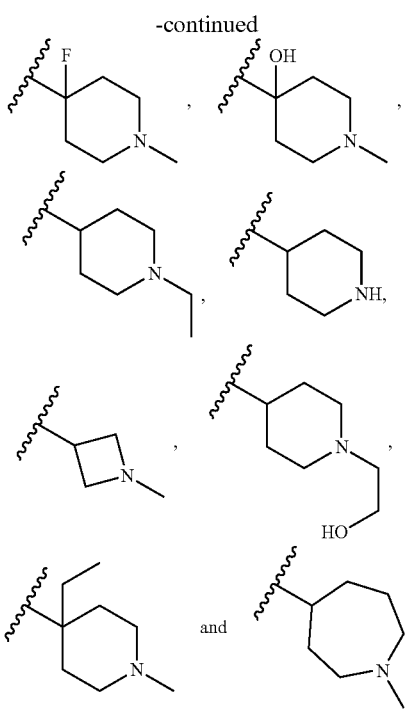

In the present disclosure, the term "amino" as used by itself or as part of another group refers to a radical of the formula —NR$^{30a}$R$^{30b}$, wherein R$^{30a}$ and R$^{30b}$ are independently hydrogen, alkyl, hydroxyalkyl, optionally substituted cycloalkyl, optionally substituted aryl, optionally substituted heterocyclo, or optionally substituted heteroaryl, or R$^{30a}$ and R$^{30b}$ are taken together to form a 3- to 8-membered optionally substituted heterocyclo. In one embodiment, R$^{30a}$ and R$^{30b}$ are independently hydrogen or C$_{1-4}$ alkyl. Non-limiting exemplary amino groups include —NH$_2$ and —N(H)(CH$_3$).

In the present disclosure, the term "(amino)alkyl" as used by itself or as part of another group refers to an alkyl group substituted with an amino group. In one embodiment, the (amino)alkyl is a C$_{1-6}$ alkyl substituted with an amino group, i.e., an (amino)C$_{1-6}$ alkyl. In another embodiment, the (amino)alkyl is an (amino)C$_{1-4}$ alkyl. Non-limiting exemplary (amino)alkyl groups include —CH$_2$NH$_2$, —CH$_2$CH$_2$NH$_2$, —CH$_2$CH$_2$N(H)CH$_3$, —CH$_2$CH$_2$N(CH$_3$)$_2$, and —CH$_2$N(H) cyclopropyl.

In the present disclosure, the term "carboxamido" as used by itself or as part of another group refers to a radical of formula —C(=O)NR$^{31a}$R$^{31b}$, wherein R$^{31a}$ and R$^{31b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{31a}$ and R$^{31b}$ taken together with the nitrogen to which they are attached form a 3- to 8-membered optionally substituted heterocyclo group. In one embodiment, R$^{31a}$ and R$^{31b}$ are each independently hydrogen or optionally substituted alkyl. In one embodiment, R$^{31a}$ and R$^{31b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, —CON(CH$_3$)$_2$, and —CON(H)Ph.

In the present disclosure, the term "amido" as used by itself or as part of another group refers to a radical of formula —N(R$^{32a}$)C(=O)R$^{32b}$, wherein R$^{32a}$ is hydrogen or C$_{1-4}$ alkyl; and R$^{32b}$ is C$_{1-6}$ alkyl, optionally substituted cycloalkyl, optionally substituted aryl, C$_{1-4}$ alkoxy, or amino. In one embodiment, R$^{32a}$ is hydrogen. In another embodiment, R$^{32b}$ is C$_{1-4}$ alkyl, C$_{1-4}$ alkoxy, or amino. Non-limiting exemplary amido groups include —N(H)C(=O)CH$_3$, —N(H)C(=O)OCH$_3$, and —N(H)C(=O)N(H)CH$_3$.

In the present disclosure, the term "sulfonamido" as used by itself or as part of another group refers to a radical of the formula —SO$_2$NR$^{8a}$R$^{8b}$, wherein Ra and Rb are each independently hydrogen, optionally substituted alkyl, or optionally substituted aryl, or R$^{8a}$ and R$^{8b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

In the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl group substituted with one or two optionally substituted heterocyclo groups. In one embodiment, the (heterocyclo)alkyl is a $C_{1-4}$ alkyl substituted with one optionally substituted heterocyclo group, i.e., a (heterocyclo)$C_{1-4}$ alkyl. In another embodiment, the (heterocyclo)alkyl is a $C_{1-4}$ alkyl substituted with one optionally substituted 4- to 8-membered heterocyclo group, i.e., a (4- to 8-membered heterocyclo)$C_{1-4}$ alkyl. In another embodiment, the (heterocyclo)alkyl is a $C_1$ alkyl substituted with one optionally substituted 4- to 8-membered heterocyclo group, i.e., (4- to 8-membered heterocyclo)-$CH_2$—. Non-limiting exemplary (heterocyclo)alkyl groups include:

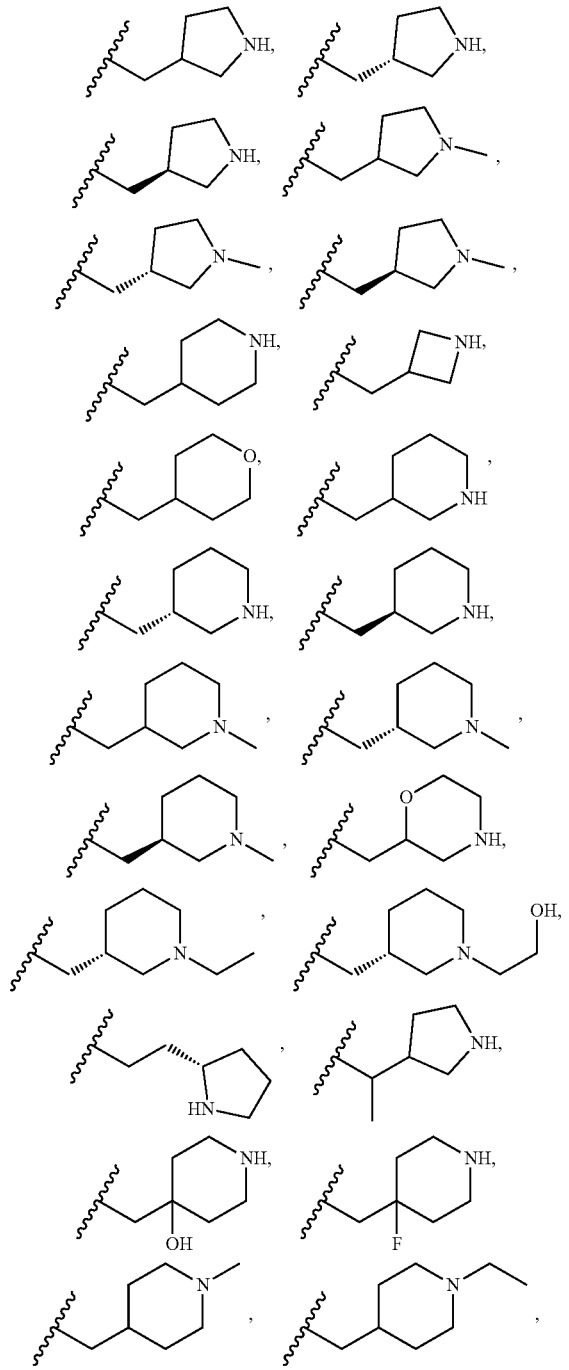

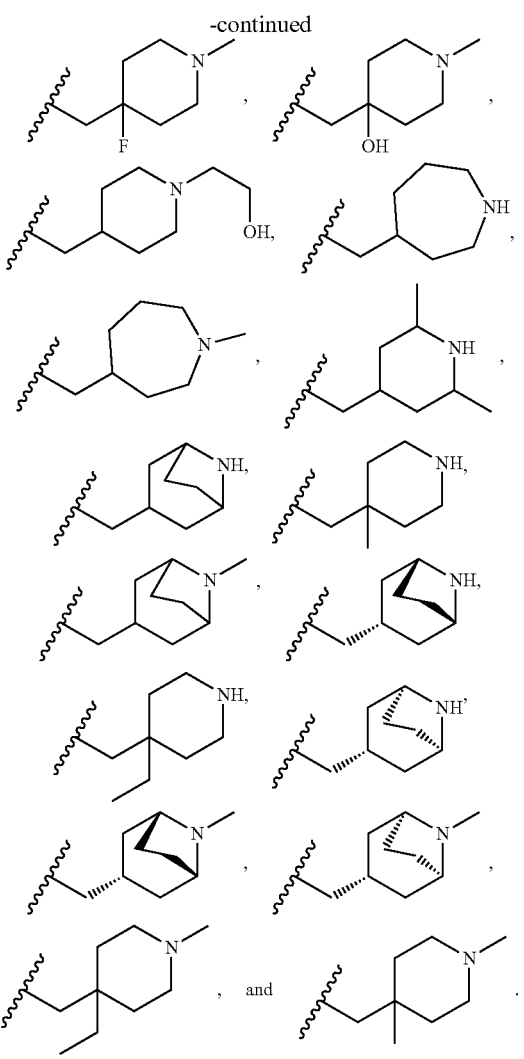

In the present disclosure, the terms "(cycloalkyl)alkyl" as used by itself or part of another group refers to an alkyl group substituted with one or two optionally substituted cycloalky groups. In one embodiment, the (cycloalkyl)alkyl is a $C_{1-4}$ alkyl substituted with one optionally substituted cycloalkyl group, i.e., a (cycloalkyl)$C_{1-4}$ alkyl. In another embodiment, the (cycloalkyl)alkyl is a $C_{1-4}$ alkyl substituted with one amino- or (alkyl)amino-substituted cycloalkyl. Non-limiting exemplary (cycloalkyl)alkyl groups include:

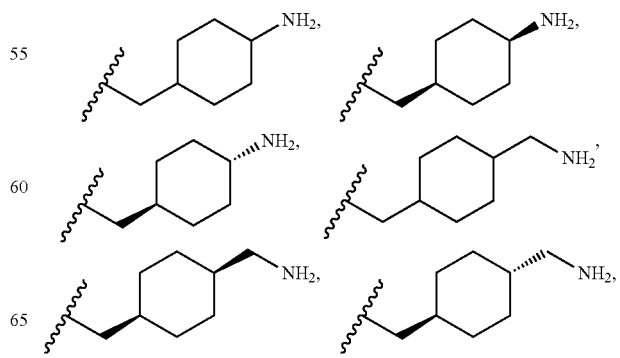

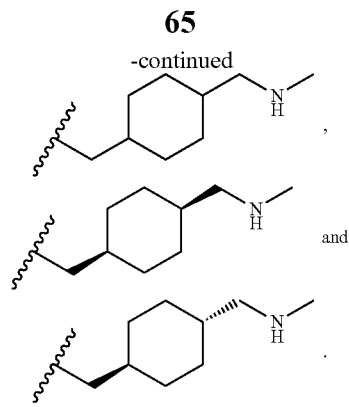

In the present disclosure, the terms "(heteroaryl)alkyl" as used by itself or part of another group refers to an alkyl group substituted with one or two optionally substituted heteroaryl groups. In one embodiment, the (heteroaryl)alkyl is a $C_{1-4}$ alkyl substituted with one optionally substituted heteroaryl group, i.e., a (heteroaryl)$C_{1-4}$ alkyl. In another embodiment, the (heteroaryl)alkyl is a $C_{1-4}$ alkyl substituted with one optionally substituted 5- or 6-membered heteroaryl group, i.e., a (5- or 6-membered heteroaryl)$C_{1-4}$ alkyl. Non-limiting exemplary (heteroaryl)alkyl groups include:

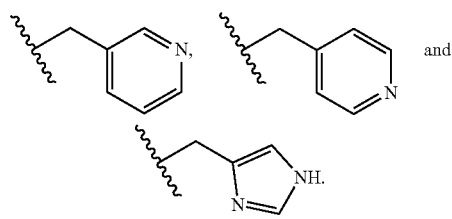

EXAMPLES

Example 1

Synthesis of 2-fluoro-4-(6-(1-methyl-H-indazol-5-yl)-3-(piperidin-4-ylmethyl)-3H-imidazo[4,5-c]pyridin-7-yl)benzonitrile (Cpd. No. 19) and 2-fluoro-4-(6-(1-methyl-1H-indazol-5-yl)-3-((1-methylpiperidin-4-yl)methyl)-3H-imidazo[4,5-c]pyridin-7-yl)benzonitrile (Cpd. No. 1)

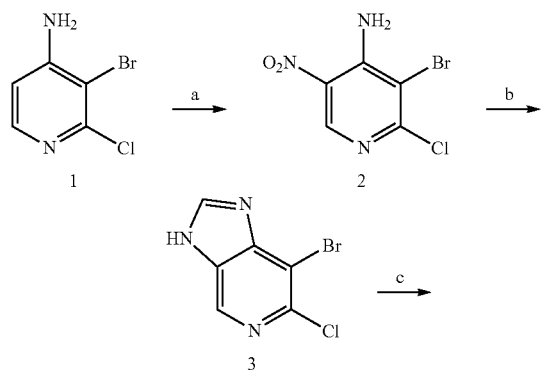

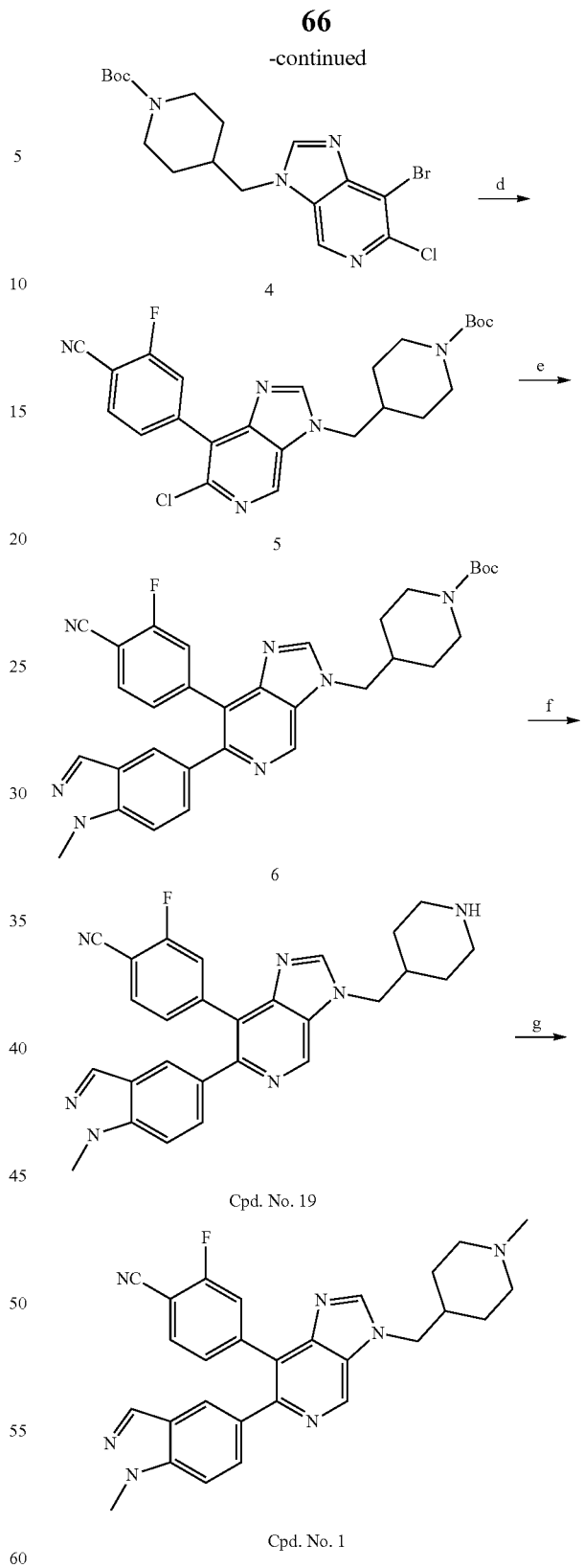

Reagents and conditions: (a) NaNO₃, Conc H₂SO₄, 0° C.-rt, Overnight, 85%; (b) Fe, CH(OEt)₃, Yb(OTf)₃, 1.0 M AcOH, 75° C., 3 h, 75%; (c) Cs₂CO₃, DMF, tert-butyl 4 ((tosyloxy)methyl)piperidine-1-carboxylate, 80° C., overnight, 60%; (d) Pd(PPh₃)₄, Na₂CO₃, (4-cyano-3-fluorophenyl)boronic acid, Dioxane:H₂O (4:1), 80° C., overnight, N₂, 70%; (e) (1-methyl-1H-indazol-5-yl)boronic acid, Pd(OAc)$_2$, X phos, K$_3$PO$_4$, nBuOH, H$_2$O, 100° C., 70%; (f) DCM/TFA (4/1), rt; (g) HCHO, AcOH, NaBH(OAc)$_3$, DCE, rt, 6 h, 90%.

Step a:

To a stirred solution of 3-bromo-2-chloropyridin-4-amine (5.00 g, 24.10 mmol) in concentrated H$_2$SO$_4$ (36 mL) at 5° C. was added KNO$_3$ (4.87 g, 48.20 mmol). The resultant solution was allowed to warm to room temperature and stir for overnight. The reaction mixture was poured onto ice chips (400 mL) giving a pale yellow precipitate. The precipitate was collected by filtration and washed with water then dried under reduced pressure. yield: (5.20 g, 85%). MS [M+H]+=251.9.

Step b:

A suspension of 3-bromo-2-chloro-5-nitropyridin-4-amine (1.50 gm, 6.0 mmol), iron (1.74 gm, 30.0 mmol), triethylorthoformate (4.58 gm, 30.0 mmol) and ytterbium (III) triflate (19 mg, 0.03 mmol) in 6 mL (1.0 M) acetic acid was stirred vigorously at 75° C. for 3 h. After cooling, the reaction mixture was added 150 mL H$_2$O and 150 mL EtOAc, filtered through celite. The organic layer was separated; the aqueous layer was extracted with EtOAc. The organic layers were combined, washed with sat. Na$_2$CO$_3$ solution, dried over Na$_2$SO$_4$, filtered and evaporated under reduced pressure. The residue was purified by flash column to furnish the desired title compound 3 in 75% yield. MS [M+H]+=232.46.

Step c:

To an ice-cooled solution of 3 (310 mg, 1.34 mmol) in 6 mL of anhydrous DMF was added Cs$_2$CO$_3$ (873 mg, 2.68 mmol). The resulting mixture was stirred 15 min, followed by addition of tert-butyl 4 ((tosyloxy)methyl)piperidine-1-carboxylate (520 mg, 1.41 mmol). Then the mixture was heated at 80° C. overnight. The reaction was quenched with saturated aq. NH$_4$Cl. The mixture was directly purified by reverse flash column (0-100% acetonitrile in water) to afford the desired compound 4 in 60% yield. MS [M+H]+=429.06.

Step d:

A mixture of 4 (105 mg, 0.25 mmol), (4-cyano-3-fluorophenyl)boronic acid (44 mg, 0.26 mmol), Pd(PPh$_3$)$_4$ (30 mg, 0.025 mmol) and Na$_2$CO$_3$ (80 mg, 0.75 mmol) in 5 mL dioxane:H$_2$O (4:1) was evacuated and refilled with nitrogen three times. The resulting mixture was stirred at 80° C. overnight and concentrated under vacuum. The residue was purified by reverse HPLC to afford the desired compound 5 in 70% yield. MS [M+H]+=470.16.

Step e:

A 50 mL of round bottle was charged with 5 (80 mg, 0.17 mmol), K$_3$PO$_4$ (18 mg, 0.84 mmol), Pd(OAc)$_2$ (0.47 mg, 2.09 µmol), Xphos (1.99 mg, 4.18 µmol) and (1-methyl-1H-indazol-5-yl)boronic acid (35 mg, 0.20 mmol). The bottle was evacuated and refilled with nitrogen three times. Then 4 mL of a mixture of solvent of nBuOH:H$_2$O (4:1) was added via syringe. The resulting mixture was evacuated and refilled with nitrogen three times. Then the mixture was heated at 100° C. for 6 h. LC-MS monitored that the starting material was completely converted. The mixture was concentrated and purified by reverse HPLC to afford the desired compound 6 in 70% yield. MS [M+H]+=566.26.

Step f:

Compound 6 (40 mg) was dissolved in 4 mL of DCM/TFA (3:1). The resulting solution was stirred at room temperature for 2 h and concentrated under vacuum. The residue was purified by reverse phase HPLC to give desired compound that was further passed through silica gel using 5% MeOH in DCM to give Cpd. No. 19. [M+H]+: 466.20. $^1$H NMR (400 MHz, Methanol-d4)$^1$H NMR (400 MHz, Methanol-d4) δ 9.39 (s, 1H), 8.75 (s, 1H), 8.07 (s, 1H), 7.89 (d, J=1.4 Hz, 1H), 7.68 (dd, J=8.1, 6.7 Hz, 1H), 7.58 (d, J=8.8 Hz, 1H), 7.49 (dd, J=10.1, 1.5 Hz, 1H), 7.38 (dd, J=8.8, 1.6 Hz, 1H), 7.27 (dd, J=8.0, 1.5 Hz, 1H), 4.54 (d, J=7.2 Hz, 2H), 4.10 (s, 3H), 3.23 (q, J=7.3 Hz, 2H), 3.09-2.93 (m, 2H), 2.45 (m, 1H), 1.94 (d, J=14.4 Hz, 2H), 1.64 (q, J=12.2 Hz, 2H).

Step g:

To a solution of Cpd. No. 19 (40 mg, 0.088 mmol) in DCE (3 mL) was added HCHO (37% aqueous solution, 35 µL, 0.354 mmol, 4 eq) and AcOH (21 µL, 0.354 mmol, 4 eq). The mixture was stirred at room temperature for 10 min then was cooled to 0° C. and Na(OAc)$_3$BH (74 mg, 0.354 mmol, 4 eq) was added. After 6 h, the solvent was removed under reduced pressure. The reaction was quenched with saturated aqueous NaHCO$_3$ then extracted with DCM. The combined organic layers were dried over Na$_2$SO$_4$ then concentrated to give a crude product that was purified by reverse HPLC to afford the desired compound that was further passed through silica gel using 5% MeOH in DCM to give Cpd. No. 1 in 90% yield. MS [M+H]+=480.22. $^1$H NMR (400 MHz, CDCl$_3$) δ 9.61 (s, 1H), 8.40 (s, 1H), 8.05 (d, J=0.9 Hz, 1H), 7.84 (s, 1H), 7.59 (dd, J=8.0, 6.5 Hz, 1H), 7.40 (d, J=8.7 Hz, 1H), 7.34 (dd, J=9.4, 1.5 Hz, 1H), 7.27-7.19 (m, 2H), 4.49 (d, J=6.9 Hz, 2H), 4.13 (s, 3H), 3.65 (d, J=11.9 Hz, 2H), 2.84 (s, 3H), 2.79-2.70 (m, 1H), 2.41-2.39 (m, 2H), 1.87 (d, J=13.8 Hz, 2H), 1.38-1.20 (m, 2H).

Example 2

Analytical Characterization of Compounds of the Disclosure

Table 3 provides $^1$H NMR and/or mass spectroscopy data for representative Compounds of the Disclosure. These compound were prepared using methodology described in EXAMPLE 1 and known in the art.

TABLE 3

| Cpd. No. | MS [M + H]+ | $^1$H NMR |
|---|---|---|
| 2 | 479.22 | |
| 3 | 495.22 | |
| 4 | 494.23 | |
| 5 | 497.18 | $^1$H NMR (400 MHz, CDCl$_3$) δ 9.08 (s, 1H), 8.12 (s, 1H), 7.91 (d, J = 1.6 Hz, 1H), 7.81 (d, J = 8.2 Hz, 1H), 7.58-7.53 (m, 1H), 7.40 (dd, J = 8.3, 1.6 Hz, 2H), 7.33 (d, J = 9.8 Hz, 1H), 4.38 (d, J = 7.2 Hz, 2H), 3.68 (d, J = 11.8 Hz, 2H), 2.87 (s, 3H), 2.83 (s, 3H), 2.73-2.67 (m, 1H), 2.41-2.39 (m, 2H), 1.87 (d, J = 13.8 Hz, 2H), 1.38-1.20 (m, 2H). |

TABLE 3-continued

| Cpd. No. | MS [M + H]+ | ¹H NMR |
|---|---|---|
| 6 | 462.23 | ¹H NMR (400 MHz, CDCl₃) δ 9.42 (s, 1H), 8.26 (s, 1H), 8.00 (d, J = 0.8 Hz, 1H), 7.82 (s, 1H), 7.65 (d, J = 8.3 Hz, 2H), 7.52 (d, J = 8.4 Hz, 2H), 7.32 (t, J = 10.8 Hz, 2H), 4.43 (d, J = 7.0 Hz, 2H), 4.11 (s, 3H), 3.66 (d, J = 11.5 Hz, 2H), 2.83 (s, 3H), 2.79-2.73 (m, 1H), 2.44-2.31 (m, 2H), 1.87 (d, J = 14.2 Hz, 2H), 1.38-1.20 (m, 2H). |
| 7 | 461.23 | |
| 8 | 497.24 | ¹H NMR (400 MHz, CDCl₃) δ 9.70 (s, 1H), 8.36 (s, 1H), 7.67 (dd, J = 8.3, 6.6 Hz, 1H), 7.41-7.29 (m, 2H), 6.83 (d, J = 8.4 Hz, 1H), 6.69 (d, J = 2.0 Hz, 1H), 6.61 (d, J = 8.4 Hz, 1H), 4.43 (d, J = 7.1 Hz, 2H), 4.26 (t, J = 4.5 Hz, 2H), 3.61 (d, J = 11.8 Hz, 2H), 3.44-3.32 (m, 2H), 2.97 (s, 3H), 2.81 (s, 3H), 2.79-2.73 (m, 1H), 2.44-2.31 (m, 2H), 1.87 (d, J = 14.2 Hz, 2H), 1.38-1.20 (m, 2H). |
| 9 | 433.21 | ¹H NMR (400 MHz, CDCl₃) δ 9.14 (s, 1H), 8.19 (s, 1H), 7.70 (d, J = 8.4 Hz, 2H), 7.62 (d, J = 8.3 Hz, 2H), 7.49 (dd, J = 8.4, 3.3 Hz, 4H), 4.40 (d, J = 7.1 Hz, 2H), 3.69 (d, J = 11.8 Hz, 2H), 2.84 (s, 3H), 2.71 (t, J = 12.5 Hz, 2H), 2.26-2.20 (m, 1H), 1.87 (d, J = 15.2 Hz, 2H), 1.28-1.20 (m, 2H). |
| 10 | 479.25 | ¹H NMR (400 MHz, CDCl₃) δ 8.37 (s, 1H), 7.73 (d, J = 8.2 Hz, 2H), 7.58-7.52 (m, 3H), 6.94-6.90 (m, 3H), 4.41 (s, 2H), 4.22 (t, J = 4.4 Hz, 2H), 3.58 (d, J = 11.4 Hz, 2H), 3.36 (t, J = 4.4 Hz, 2H), 2.94 (s, 3H), 2.82 (s, 3H), 2.79-2.73 (m, 1H), 2.44-2.31 (m, 2H), 1.87 (d, J = 14.2 Hz, 2H), 1.38-1.20 (m, 2H). |
| 11 | 476.25 | |
| 12 | 480.22 | ¹H NMR (400 MHz, Methanol-d₄) δ 9.28 (s, 1H), 8.65 (s, 1H), 8.25 (s, 1H), 7.74 (s, 1H), 7.72-7.63 (m, 1H), 7.60 (d, J = 9.0 Hz, 1H), 7.47 (d, J = 10.0 Hz, 1H), 7.29 (dd, J = 8.8, 1.9 Hz, 2H), 4.53 (d, J = 7.2 Hz, 2H), 4.26 (s, 3H), 3.64-3.52 (m, 2H), 3.06-3.00 (m, 2H), 2.83 (s, 3H), 2.41 (m, 1H), 1.98 (d, J = 13.9 Hz, 2H), 1.81-1.64 (m, 2H). |
| 13 | 462.23 | ¹H NMR (400 MHz, Methanol-d₄) δ 9.60 (s, 1H), 8.96 (s, 1H), 8.35 (d, J = 0.9 Hz, 1H), 7.90 (dd, J = 1.8, 0.9 Hz, 1H), 7.79-7.69 (m, 2H), 7.66-7.55 (m, 3H), 7.22 (dd, J = 9.0, 1.7 Hz, 1H), 4.60 (d, J = 7.3 Hz, 2H), 4.26 (s, 3H), 3.60 (d, J = 12.4 Hz, 2H), 3.09-2.94 (m, 2H), 2.89 (s, 3H), 2.43 (td, J = 8.1, 4.1 Hz, 1H), 1.98 (d, J = 13.9 Hz, 2H), 1.81-1.64 (m, 2H). |
| 14 | 452.20 | ¹H NMR (400 MHz, Methanol-d₄) δ 9.57 (s, 1H), 8.95 (s, 1H), 7.84-7.76 (m, 2H), 7.65-7.57 (m, 2H), 6.90 (dt, J = 16.2, 1.1 Hz, 3H), 6.05 (s, 2H), 4.58 (d, J = 7.3 Hz, 2H), 3.63-3.55 (m, 2H), 3.01 (td, J = 11.6, 10.3, 3.7 Hz, 2H), 2.88 (s, 3H), 2.42 (ddt, J = 11.9, 7.8, 3.9 Hz, 1H), 1.96 (d, J = 14.3 Hz, 2H), 1.74 (qd, J = 13.8, 4.0 Hz, 2H). |
| 15 | 470.19 | ¹H NMR (400 MHz, Methanol-d₄) δ 9.40 (s, 1H), 8.79 (s, 1H), 7.78 (dd, J = 8.0, 6.7 Hz, 1H), 7.49 (dd, J = 10.1, 1.5 Hz, 1H), 7.33 (dd, J = 8.0, 1.5 Hz, 1H), 6.91-6.86 (m, 3H), 6.04 (s, 2H), 4.54 (d, J = 7.3 Hz, 2H), 3.58 (d, J = 12.3 Hz, 2H), 3.01 (t, J = 12.4 Hz, 2H), 2.88 (s, 3H), 2.41 (m, 1H), 1.96 (t, J = 7.1 Hz, 2H), 1.70 (q, J = 13.9, 13.2 Hz, 2H). |
| 16 | 466.2077 | ¹H NMR (400 MHz, Methanol-d₄) δ 9.67 (s, 1H), 9.03 (s, 1H), 8.13 (d, J = 0.9 Hz, 1H), 7.99 (dd, J = 1.7, 0.8 Hz, 1H), 7.72 (dd, J = 8.1, 6.7 Hz, 1H), 7.69-7.61 (m, 1H), 7.54 (dd, J = 9.9, 1.5 Hz, 1H), 7.38 (dd, J = 8.8, 1.7 Hz, 1H), 7.31 (dd, J = 8.1, 1.5 Hz, 1H), 4.77 (d, J = 7.6 Hz, 2H), 4.12 (s, 3H), 3.86-3.66 (m, 2H), 3.46-3.40 (m, 1H), 3.28-3.08 (m, 2H), 3.01 (s, 3H), 2.40-2.35 (m, 1H), 2.13-2.03 (m, 1H). |
| 17 | 469.2074 | ¹H NMR (400 MHz, Methanol-d₄) δ 9.55 (s, 1H), 8.98 (s, 1H), 7.81 (dd, J = 8.1, 6.7 Hz, 1H), 7.52 (dd, J = 10.0, 1.5 Hz, 1H), 7.37 (dd, J = 8.1, 1.5 Hz, 1H), 6.89-6.76 (m, 2H), 6.72 (d, J = 8.4 Hz, 1H), 4.78-4.63 (m, 2H), 4.30-4.17 (m, 2H), 3.54 (ddd, J = 8.4, 6.9, 4.2 Hz, 2H), 3.41-3.36 (m, 3H), 3.23-3.10 (m, 2H), 2.96 (s, 3H), 2.24 (ddt, J = 14.2, 7.2, 3.6 Hz, 1H), 2.03-1.82 (m, 1H). |
| 18 | 483.2230 | ¹H NMR (400 MHz, Methanol-d₄) δ 9.53 (s, 1H), 8.97 (s, 1H), 7.81 (dd, J = 8.1, 6.7 Hz, 1H), 7.52 (dd, J = 10.0, 1.5 Hz, 1H), 7.37 (dd, J = 8.1, 1.5 Hz, 1H), 6.90-6.78 (m, 2H), 6.72 (d, J = 8.4 Hz, 1H), 4.72-4.68 (m, 2H), 4.31-4.19 (m, 2H), 3.54 (ddd, J = 8.4, 6.9, 4.2 Hz, 2H), 3.41-3.36 (m, 3H), 3.23-3.10 (m, 2H), 3.06 (s, 3H), 2.96 (s, 3H), 2.24 (m, 1H), 2.03-1.82 (m, 1H). |
| 20 | 448.2171 | ¹H NMR (400 MHz, Methanol-d₄) δ 9.64 (s, 1H), 8.98 (s, 1H), 8.11 (s, 1H), 7.98 (d, J = 1.5 Hz, 1H), 7.78-7.67 (m, 2H), 7.60 (t, J = 8.1 Hz, 3H), 7.35 (dd, J = 8.8, 1.6 Hz, 1H), 4.60 (d, J = 7.3 Hz, 2H), 4.10 (s, 3H), 3.48 (dt, J = 13.0, 3.1 Hz, 2H), 3.03 (td, J = 13.1, 3.0 Hz, 2H), 2.48 (ddd, J = 11.7, 7.8, 3.8 Hz, 1H), 1.93 (s, 2H), 1.68 (qd, J = 13.3, 4.0 Hz, 2H). |
| 21 | 480.2234 | ¹H NMR (400 MHz, Methanol-d₄) δ 9.44 (s, 1H), 8.80 (s, 1H), 8.08 (d, J = 0.9 Hz, 1H), 7.91 (d, J = 1.2 Hz, 1H), 7.69 (dd, J = 8.0, 6.7 Hz, 1H), 7.60 (d, J = 8.7 Hz, 1H), 7.50 (dd, J = 10.1, 1.5 Hz, 1H), 7.38 (dd, J = 8.8, 1.7 Hz, 1H), 7.28 (dd, J = 8.1, 1.5 Hz, 1H), 4.52 |

TABLE 3-continued

| Cpd. No. | MS [M + H]+ | ¹H NMR |
|---|---|---|
| | | (d, J = 7.4 Hz, 2H), 4.11 (s, 3H), 3.43 (dd, J = 12.1, 5.9 Hz, 2H), 3.22 (q, J = 12.8, 11.5 Hz, 2H), 2.48 (m, 1H), 2.11-1.70 (m, 5H), 1.52 (q, J = 11.6, 10.8 Hz, 1H). |
| 22 | 462.2328 | ¹H NMR (400 MHz, Methanol-d₄) δ 9.54 (s, 1H), 8.90 (s, 1H), 8.09 (s, 1H), 7.94 (d, J = 1.5 Hz, 1H), 7.83-7.66 (m, 2H), 7.58 (dd, J = 8.5, 4.7 Hz, 3H), 7.34 (dd, J = 8.8, 1.7 Hz, 1H), 4.53 (d, J = 7.5 Hz, 2H), 4.10 (s, 3H), 3.47-3.37 (m, 2H), 3.28-3.10 (m, 2H), 2.62-2.38 (m, 1H), 2.17-1.68 (m, 5H), 1.62-1.37 (m, 1H). |
| 23 | 497.2387 | ¹H NMR (400 MHz, Methanol-d₄) δ 9.40 (s, 1H), 8.84 (s, 1H), 7.80 (dd, J = 8.1, 6.7 Hz, 1H), 7.50 (dd, J = 10.1, 1.5 Hz, 1H), 7.35 (dd, J= 8.1, 1.5 Hz, 1H), 6.79 (dq, J = 4.0, 2.2 Hz, 2H), 6.70 (d, J = 9.0 Hz, 1H), 4.49 (d, J = 7.5 Hz, 2H), 4.30-4.19 (m, 2H), 3.40-3.30 (s, 3H), 3.26-3.10 (m, 2H), 2.95 (s, 3H), 2.50-2.40 (m, 1H), 2.12-1.66 (m, 6H), 1.58-1.42 (m, 1H). |
| 24 | 479.2481 | ¹H NMR (400 MHz, Methanol-d₄) δ 9.47 (s, 1H), 8.90 (s, 1H), 7.88-7.75 (m, 2H), 7.67-7.54 (m, 2H), 6.84-6.75 (m, 2H), 6.69 (d, J = 8.4 Hz, 1H), 4.51 (d, J = 7.5 Hz, 2H), 4.33-4.16 (m, 2H), 3.42 (ddd, J = 13.9, 6.4, 2.6 Hz, 1H), 3.39-3.35 (m, 2H), 3.29-3.10 (m, 2H), 2.95 (s, 3H), 2.46 (ddd, J = 10.6, 7.0, 3.6 Hz, 1H), 2.14-1.68 (m, 6H), 1.59-1.44 (m, 1H). |
| 25 | 483.2230 | ¹H NMR (400 MHz, Methanol-d₄) δ 9.49 (s, 1H), 8.91 (s, 1H), 7.80 (dd, J = 8.0, 6.7 Hz, 1H), 7.51 (dd, J = 10.0, 1.5 Hz, 1H), 7.36 (dd, J = 8.0, 1.5 Hz, 1H), 6.89-6.78 (m, 2H), 6.72 (d, J = 8.3 Hz, 1H), 4.55 (d, J = 7.4 Hz, 2H), 4.32-4.18 (m, 2H), 3.55-3.43 (m, 2H), 3.41-3.35 (m, 2H), 3.02 (dd, J = 12.9, 3.0 Hz, 2H), 2.96 (s, 3H), 2.43 (ddt, J = 11.6, 7.6, 3.8 Hz, 1H), 1.92 (d, J = 13.8 Hz, 2H), 1.72-1.55 (m, 2H). |
| 26 | 465.2325 | ¹H NMR (400 MHz, Methanol-d₄) δ 9.50 (s, 1H), 8.92 (s, 1H), 7.88-7.74 (m, 2H), 7.69-7.55 (m, 2H), 6.85-6.74 (m, 2H), 6.69 (d, J = 8.4 Hz, 1H), 4.55 (d, J = 7.3 Hz, 2H), 4.33-4.17 (m, 2H), 3.55-3.42 (m, 2H), 3.41-3.34 (m, 2H), 3.02 (dd, J = 13.0, 3.0 Hz, 2H), 2.95 (s, 3H), 2.44 (ddq, J = 11.6, 7.6, 3.9 Hz, 1H), 1.98-1.86 (m, 2H), 1.64 (qd, J = 13.2, 4.1 Hz, 2H). |
| 27 | 452.1921 | ¹H NMR (400 MHz, Methanol-d₄) δ 9.29 (s, 1H), 8.64 (s, 1H), 8.17 (d, J = 2.0 Hz, 1H), 8.06 (d, J = 2.1 Hz, 1H), 7.69 (dd, J = 8.0, 6.8 Hz, 1H), 7.53-7.38 (m, 2H), 7.26 (dd, J = 8.0, 1.5 Hz, 1H), 6.53 (d, J = 3.5 Hz, 1H), 4.67 (t, J = 6.7 Hz, 2H), 3.89 (s, 3H), 3.66-3.41 (m, 3H), 3.23-3.06 (m, 2H), 2.32-2.13 (m, 1H), 1.98-1.88 (m, 1H). |
| 28 | 456.1758 | 1H NMR (400 MHz, Methanol-d₄) δ 9.44 (s, 1H), 8.84 (s, 1H), 7.78 (dd, J = 8.0, 6.7 Hz, 1H), 7.49 (dd, J = 10.0, 1.5 Hz, 1H), 7.33 (dd, J = 8.0, 1.5 Hz, 1H), 6.95 (d, J = 2.1 Hz, 1H), 6.89 (d, J = 8.4 Hz, 1H), 6.82 (dd, J = 8.4, 2.1 Hz, 1H), 4.77-4.59 (m, 2H), 4.29 (td, J = 5.4, 3.8 Hz, 4H), 3.61-3.43 (m, 2H), 3.39-3.30 (m, 1H), 3.16 (dq, J = 15.4, 8.1 Hz, 2H), 2.23 (dq, J = 12.4, 6.9 Hz, 1H), 2.00-1.85 (m, 1H). |
| 29 | 469.2074 | ¹H NMR (400 MHz, Methanol-d₄) δ 9.49 (s, 1H), 8.90 (s, 1H), 7.80 (dd, J = 8.1, 6.7 Hz, 1H), 7.51 (dd, J = 10.1, 1.5 Hz, 1H), 7.37 (dd, J = 8.0, 1.5 Hz, 1H), 6.76 (d, J = 8.1 Hz, 1H), 6.71-6.61 (m, 2H), 4.79-4.63 (m, 2H), 4.35-4.28 (m, 2H), 3.58-3.50 (m, 2H), 3.41-3.34 (m, 1H), 3.32-3.25 (m, 2H), 3.21 (d, J = 8.4 Hz, 2H), 2.75 (s, 3H), 2.24 (tt, J = 12.5, 5.8 Hz, 1H), 1.94 (dq, J = 13.1, 8.4 Hz, 1H). |
| 30 | 434.2015 | ¹H NMR (400 MHz, Methanol-d₄) δ 9.65 (s, 1H), 9.02 (s, 1H), 8.11 (d, J = 0.9 Hz, 1H), 7.97 (dd, J = 1.6, 0.8 Hz, 1H), 7.77-7.69 (m, 2H), 7.65-7.55 (m, 3H), 7.35 (dd, J = 8.8, 1.7 Hz, 1H), 4.84-4.68 (m, 2H), 4.11 (s, 3H), 3.57 (tt, J = 8.8, 4.6 Hz, 2H), 3.43-3.33 (m, 1H), 3.21-3.15 (m, 2H), 2.27 (dq, J = 12.4, 6.7 Hz, 1H), 2.04-1.90 (m, 1H). |
| 31 | 448.2171 | ¹H NMR (400 MHz, Methanol-d₄) δ 9.63 (q, J = 1.7 Hz, 1H), 9.00 (d, J = 2.3 Hz, 1H), 8.10 (d, J = 0.9 Hz, 1H), 7.96 (s, 1H), 7.77-7.68 (m, 2H), 7.68-7.50 (m, 3H), 7.35 (dd, J = 8.8, 1.7 Hz, 1H), 4.76 (d, J = 7.1 Hz, 2H), 4.10 (s, 3H), 3.96-3.66 (m, 2H), 3.37-3.34 (m, 2H), 3.17-3.20 (m, 1H), 3.01 (s, 3H), 2.38-2.30 (m, 1H), 2.07-1.96 (m, 1H). |
| 32 | 451.2168 | ¹H NMR (400 MHz, Methanol-d₄) δ 9.54 (s, 1H), 8.97 (s, 1H), 7.83-7.76 (m, 2H), 7.65-7.57 (m, 2H), 6.84-6.74 (m, 2H), 6.69 (d, J = 8.5 Hz, 1H), 4.79-4.64 (m, 2H), 4.28-4.21 (m, 2H), 3.55 (dq, J = 12.0, 4.8 Hz, 2H), 3.42-3.30 (m, 3H), 3.26-3.11 (m, 2H), 2.95 (s, 3H), 2.25 (dtd, J = 11.9, 7.3, 4.6 Hz, 1H), 1.94 (dq, J = 13.0, 8.4 Hz, 1H). |
| 33 | 465.2325 | ¹H NMR (400 MHz, Methanol-d₄) δ 9.48 (d, J = 6.2 Hz, 1H), 8.93 (d, J = 4.8 Hz, 1H), 7.87-7.73 (m, 2H), 7.66-7.54 (m, 2H), 6.83-6.75 (m, 2H), 6.69 (d, J = 8.2 Hz, 1H), 4.71 (brs, 2H), 4.33-4.19 (m, 2H), 3.84-3.77 (m, 2H), 3.36-3.30 (m, 3H), 3.25-3.10 (m, 2H), 3.00 (s, 3H), 2.95 (s, 3H), 2.39-2.25 (m, 1H), 2.21-1.89 (m, 1H). |

Example 3

LSD1 Activity

Human recombinant LSD1 protein expressed in *E. coli* cells was purchased from Active Motif (Carlsbad, Calif.). Biotin-labeled Histone H3K4Me peptide (residues 1-21 with Lys 4 monomethylated) substrate was purchased from Anaspec (Fremont, Calif.). Enzymatic activity was assessed using the AlphaLISA technology from Perkin Elmer Life Sciences (Waltham, Mass.). 2.5 μL of compound solution and 5 μL of LSD1 solutions in the assay buffer (50 mM Tris, pH 9.0, 50 mM NaCl with 0.01% Tween20 and 1 mM DTT added right before the assay) were added into a white low volume 384 well microtiter plate. This mixture solution was incubated for 15 minutes with gentle shaking at room temperature. Demethylation reaction was initiated by adding 2.5 μL of Biotin-H3K4Me peptide substrate solution in the assay buffer. Final concentrations of LSD1, Biotin-H3K4Me peptide substrate, and DMSO were 4 nM, 80 nM, and 1%, respectively. The reaction was allowed to proceed for 60 minutes in dark with gentle shaking at room temperature, after which 5 μL of Anti-H3K4 AlphaLISA acceptor beads in detection buffer from the manufacturer was added into the reaction mixture followed by incubation for 60 minutes. 10 μL of Streptavidin labeled AlphaLISA donor beads in detection buffer was added into the mixture followed by 30-minute incubation. Final acceptor and donor beads concentrations were both at 10 μg/mL. Plates were read on a BMG CLARIOStar multimode plate reader from BMG Labtech (Ortenberg, Germany) with an excitation wavelength of 680 nm and emission wavelength of 615 nm. $IC_{50}$ values of inhibitors were obtained by fitting the fluorescence intensity vs inhibitor concentrations in a sigmoidal dose-response curve (variable slope) with a non-linear regression using Prism 7 (La Jolla, Calif.).

The LSD1 inhibitory activity of representative Compounds of the Disclosure are provided in Table 4.

TABLE 4

| Cpd. No. | LSD1 IC50 (nM) |
|---|---|
| 1 | 40.1 |
| 2 | 237 |
| 3 | 219.8 |
| 4 | 371.8 |
| 5 | 928.2 |
| 6 | 66.26 |
| 7 | 68.03 |
| 8 | 16.22 |
| 9 | >1000 |
| 10 | 53.07 |
| 11 | 116.5 |
| 12 | 97.64 |
| 13 | 114.6 |
| 14 | 15.7 |
| 15 | 27.75 |
| 16 | 27.96 |
| 17 | 12.08 |
| 18 | 12.02 |
| 19 | 11.77 |
| 20 | 13.73 |
| 21 | 17.27 |
| 22 | 16.24 |
| 23 | 12.96 |
| 24 | 10.99 |
| 25 | 8.01 |
| 26 | 14.70 |
| 27 | 53.34 |
| 28 | 9.57 |

TABLE 4-continued

| Cpd. No. | LSD1 IC50 (nM) |
|---|---|
| 29 | 47.03 |
| 30 | 39.76 |
| 31 | 87.25 |
| 32 | 5.67 |
| 33 | 29.46 |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound having Formula II:

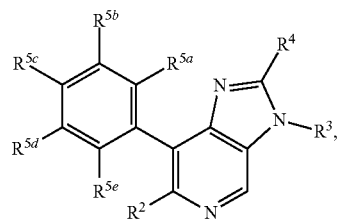

II or a pharmaceutically acceptable salt or solvate thereof, wherein:

$R^2$ is selected from the group consisting of optionally substituted $C_6$-$C_{14}$ aryl and optionally substituted 5- to 14-membered heteroaryl;

$R^3$ is selected from the group consisting of optionally substituted $C_{1-6}$ alkyl, (amino)alkyl, (heterocyclo)alkyl, (cycloalkyl)alkyl, and —C(═O)$R^{3a}$;

$R^{3a}$ is optionally substituted heterocyclo;

$R^4$ is selected from the group consisting of hydrogen and $C_{1-6}$ alkyl; and $R^{5a}$, $R^{5b}$, $R^{5c}$, $R^{5d}$, and $R^{5e}$ are each independently selected from the group consisting of hydrogen, halo, cyano, amino, hydroxy, $C_{1-4}$ alkyl, $C_{1-4}$ haloalkyl, and $C_{1-4}$ alkoxy;

with proviso that said compound having Formula II is not (R)-2-fluoro-4-(6-(1-methyl-1H-indazol-5-yl)-3-(pyrrolidin-3-ylmethyl)-3H-imidazo[4,5-c]pyridin-7-yl) benzonitrile.

2. The compound of claim 1, or a pharmaceutically acceptable salt or solvate thereof, wherein:

$R^2$ is:

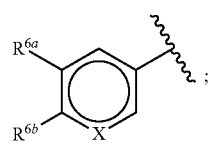

$R^{6a}$ and $R^{6b}$ are independently selected from the group consisting of hydrogen, halo, cyano, amino, hydroxy, $C_{1-4}$ alkyl, $C_{1-4}$ haloalkyl, and $C_{1-4}$ alkoxy; or $R^{6a}$ and $R^{6b}$ taken together with the carbon atoms to which they are attached form a fused optionally substituted 5- or 6-membered heterocyclic group or optionally substituted 5- or 6-membered heteroaromatic group; and X is selected from the group consisting of —CH= and —N=.

3. The compound of claim 1, or a pharmaceutically acceptable salt or solvate thereof, wherein $R^2$ is selected from the group consisting of:

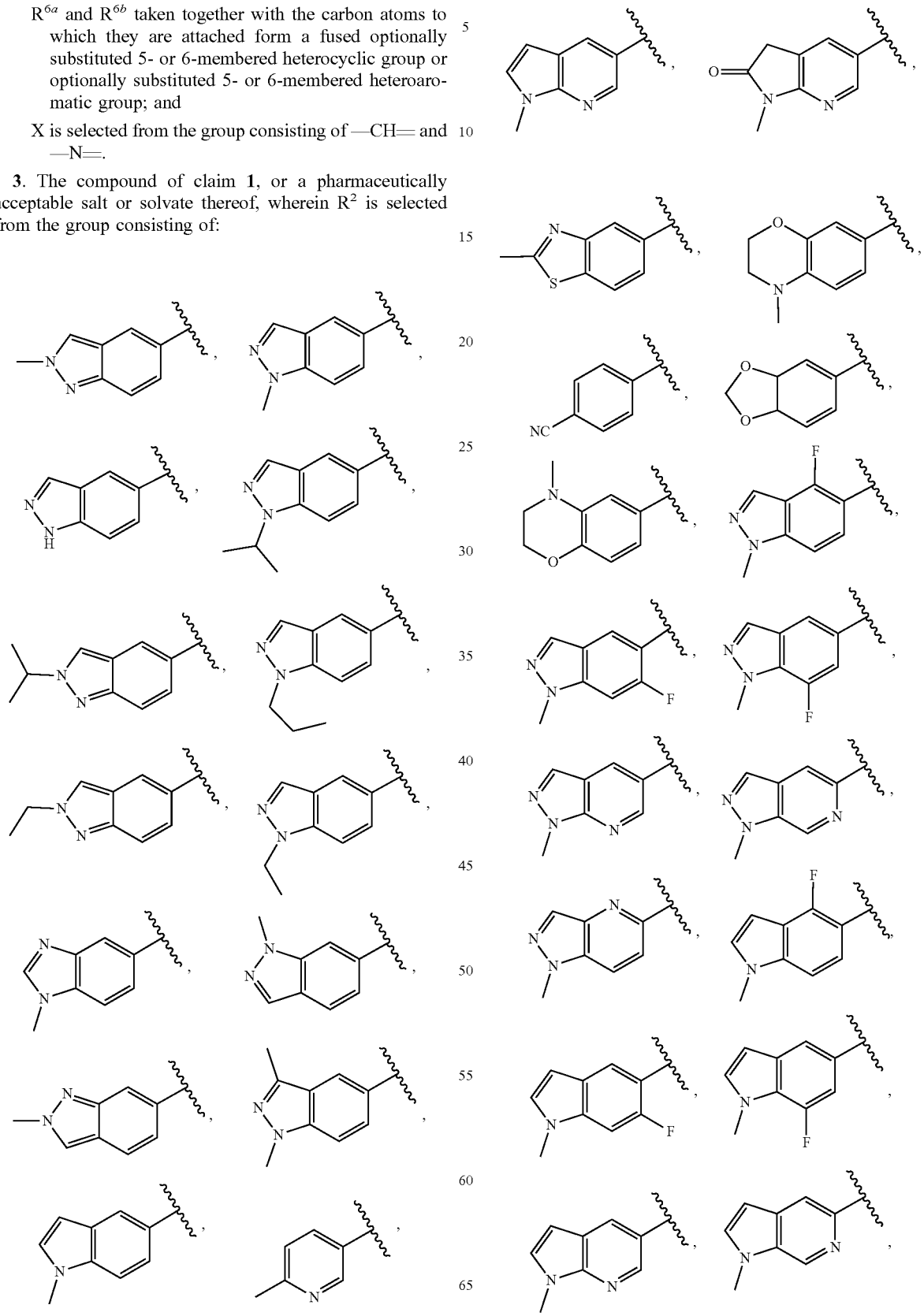

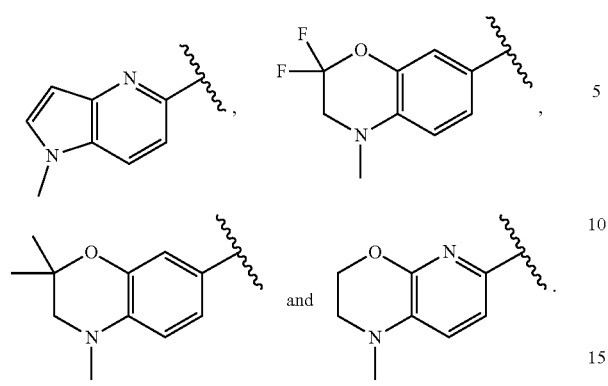
4. The compound of claim 1, or a pharmaceutically acceptable salt or solvate thereof, wherein $R^3$ is (heterocyclo)-$CH^2$—.
5. The compound of claim 4, or a pharmaceutically acceptable salt or solvate thereof, wherein $R^3$ is selected from the group consisting of:
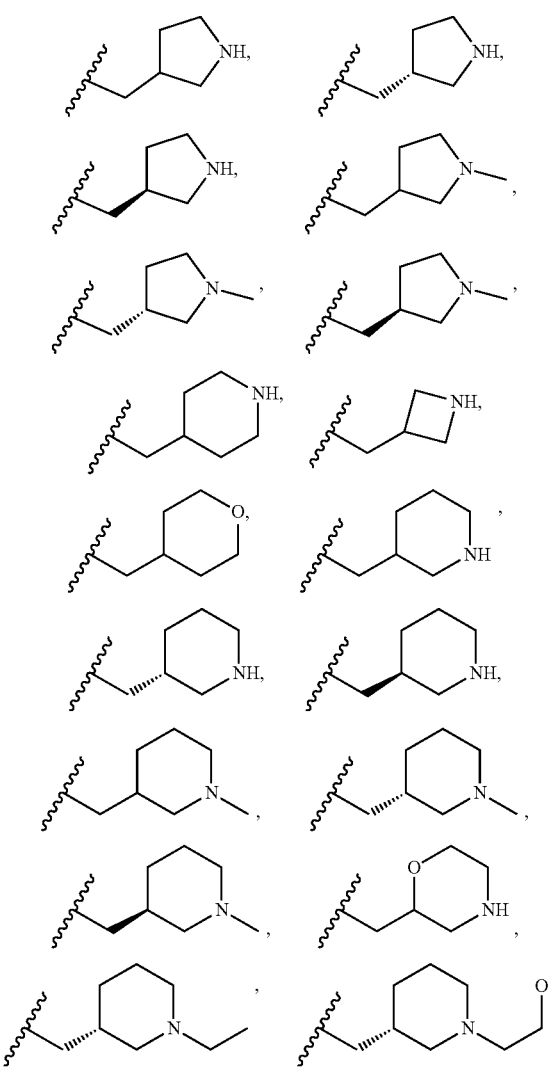
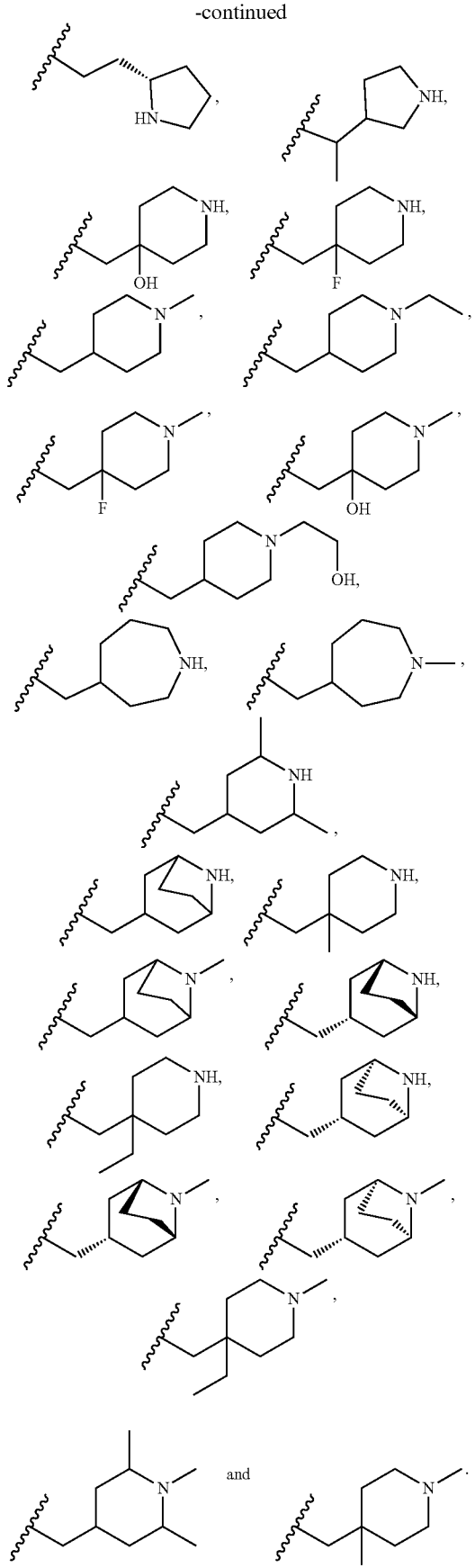

6. The compound of claim 1 having Formula III:

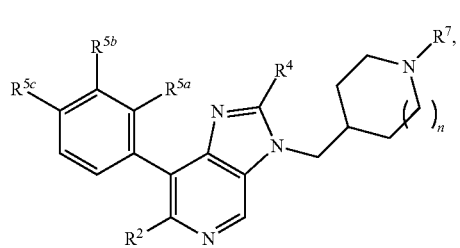

or a pharmaceutically acceptable salt or solvate thereof, wherein:
R⁷ is selected from the group consisting of hydrogen and C$_{1-4}$ alkyl; and
n is 0, 1, or 2.

7. The compound of claim 6, or a pharmaceutically acceptable salt thereof, wherein R⁷ is hydrogen or C$_{1-4}$ alkyl.

8. The compound of claim 1 having Formula VI:

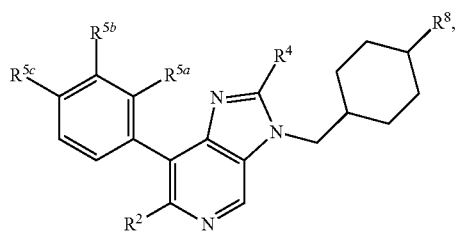

or a pharmaceutically acceptable salt or solvate thereof, wherein R⁸ is selected from the group consisting of amino and (amino)alkyl.

9. The compound of claim 1, or a pharmaceutically acceptable salt or solvate thereof, selected from the group consisting of

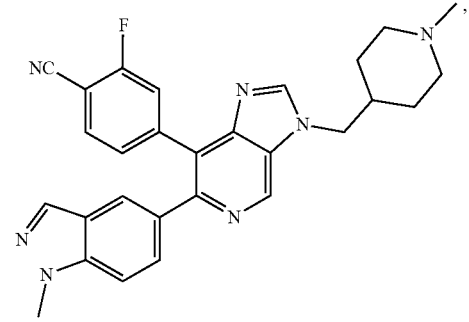

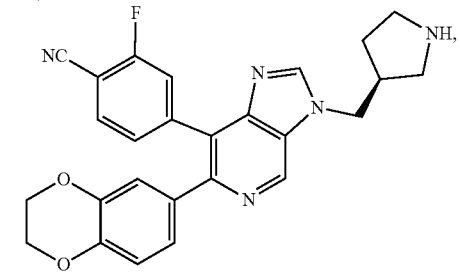

-continued

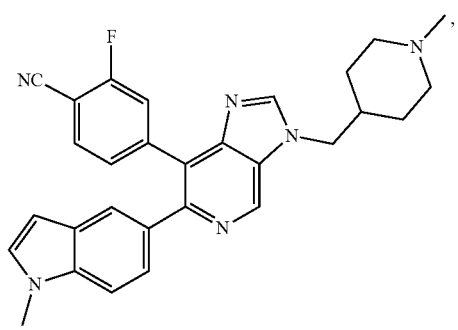

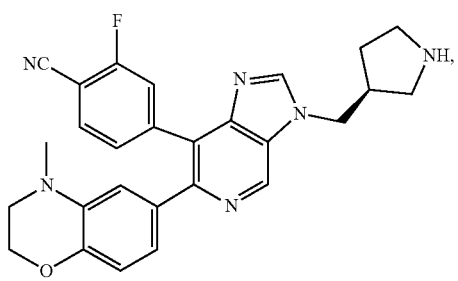

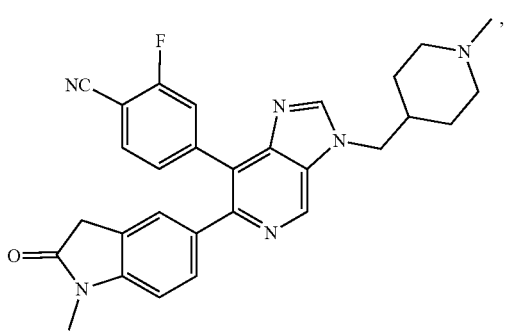

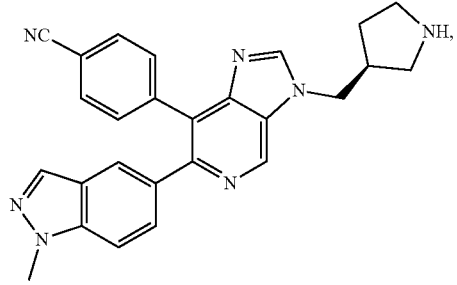

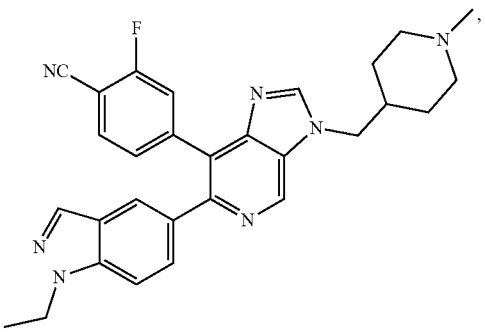

81
-continued
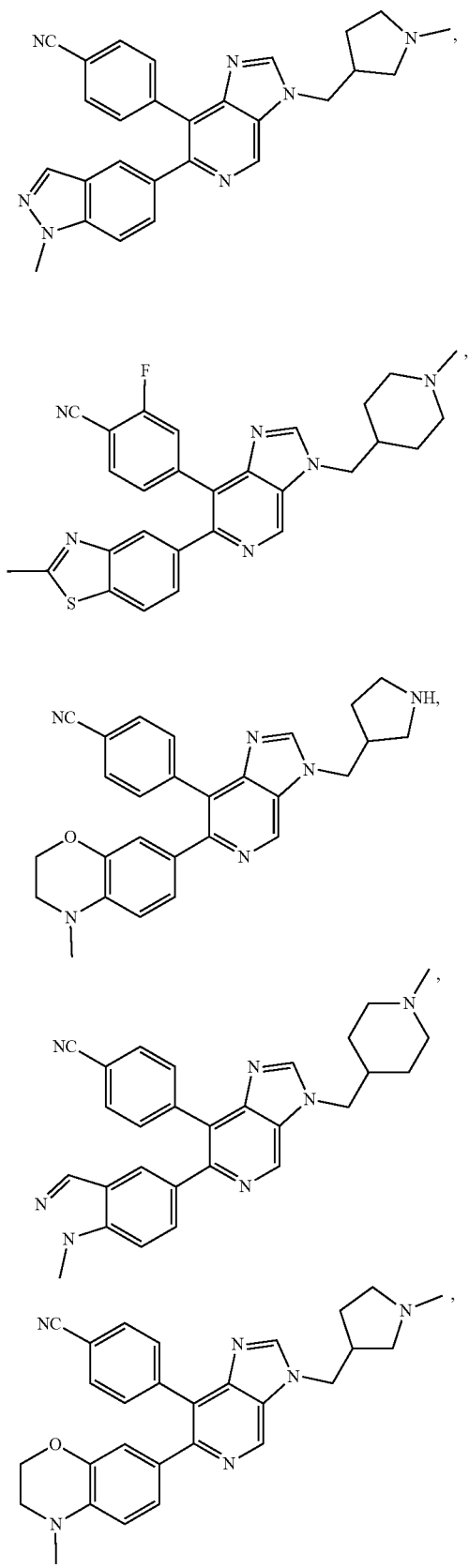
82
-continued
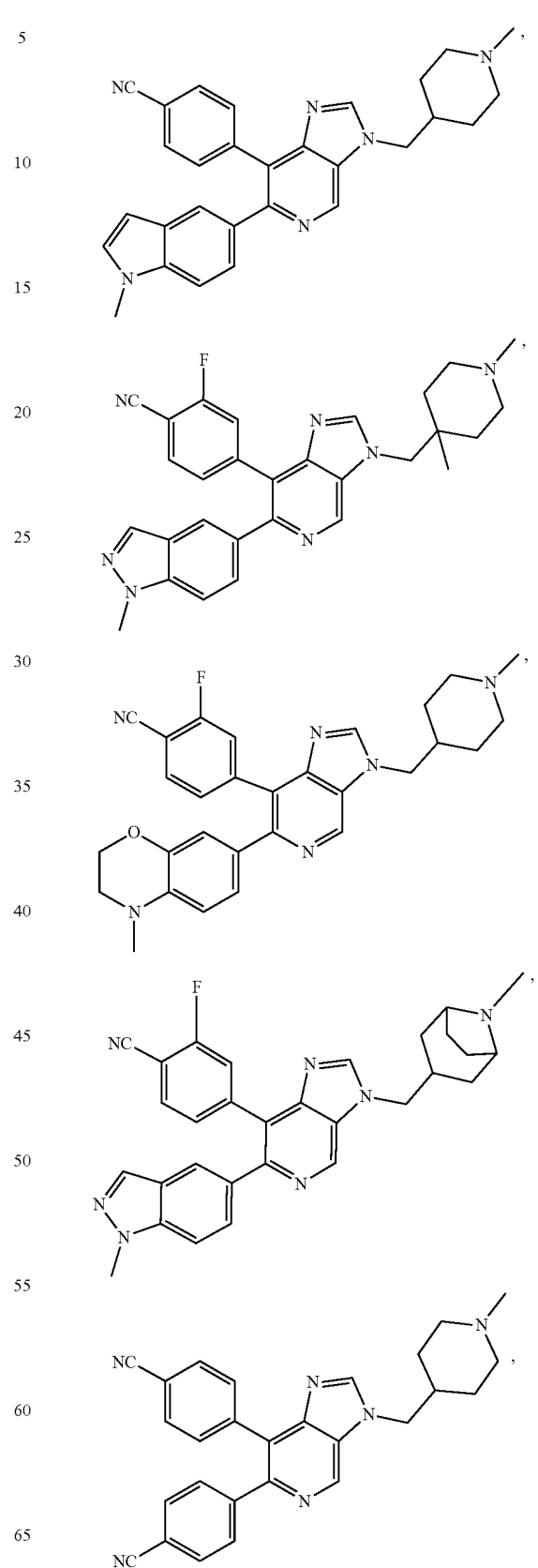

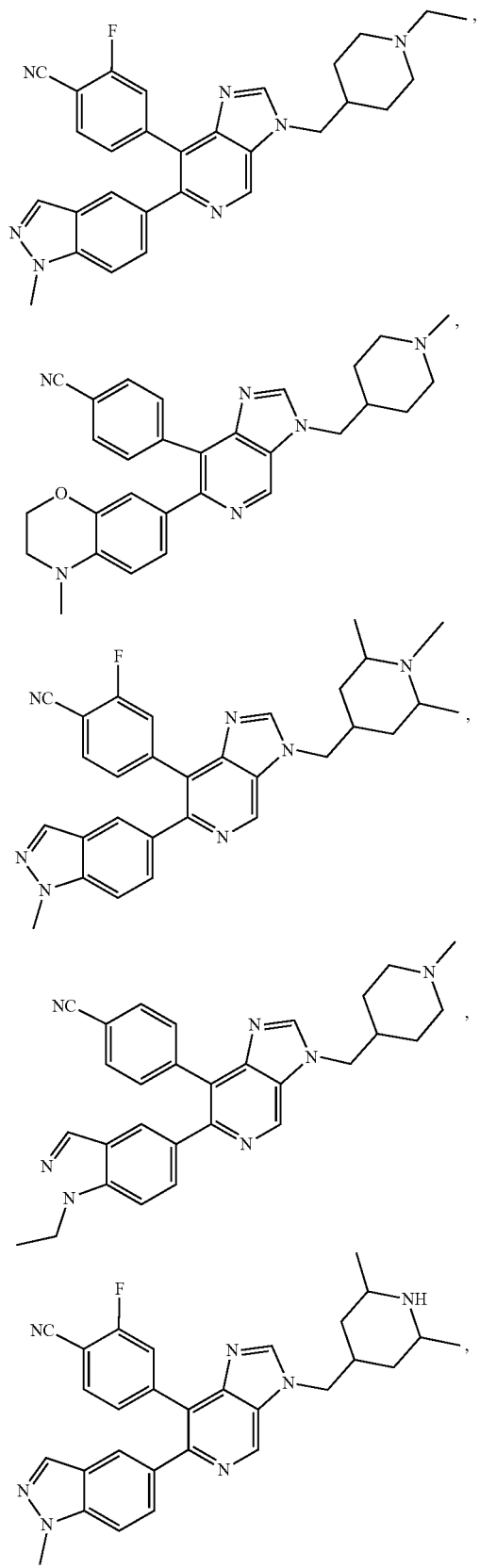
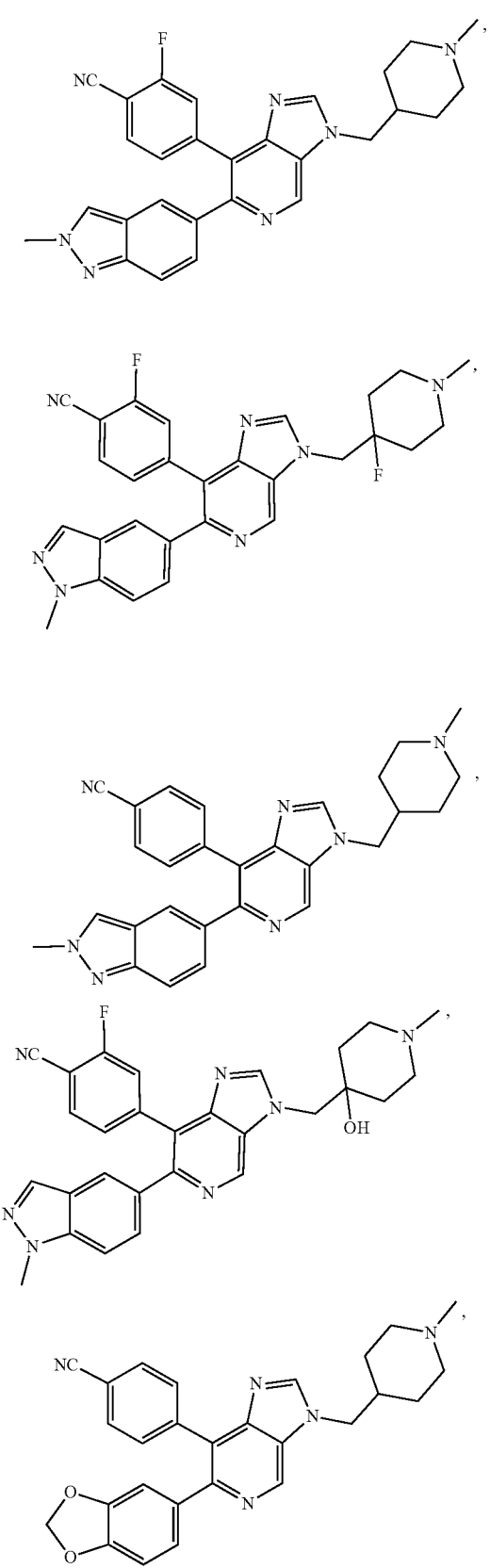

85
-continued
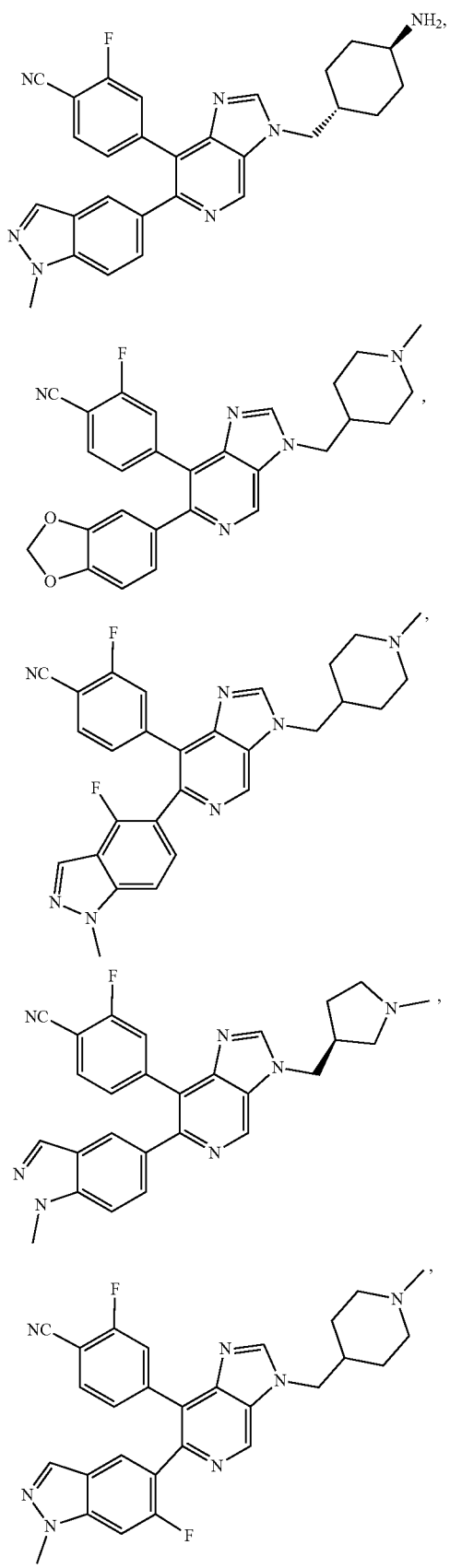
86
-continued
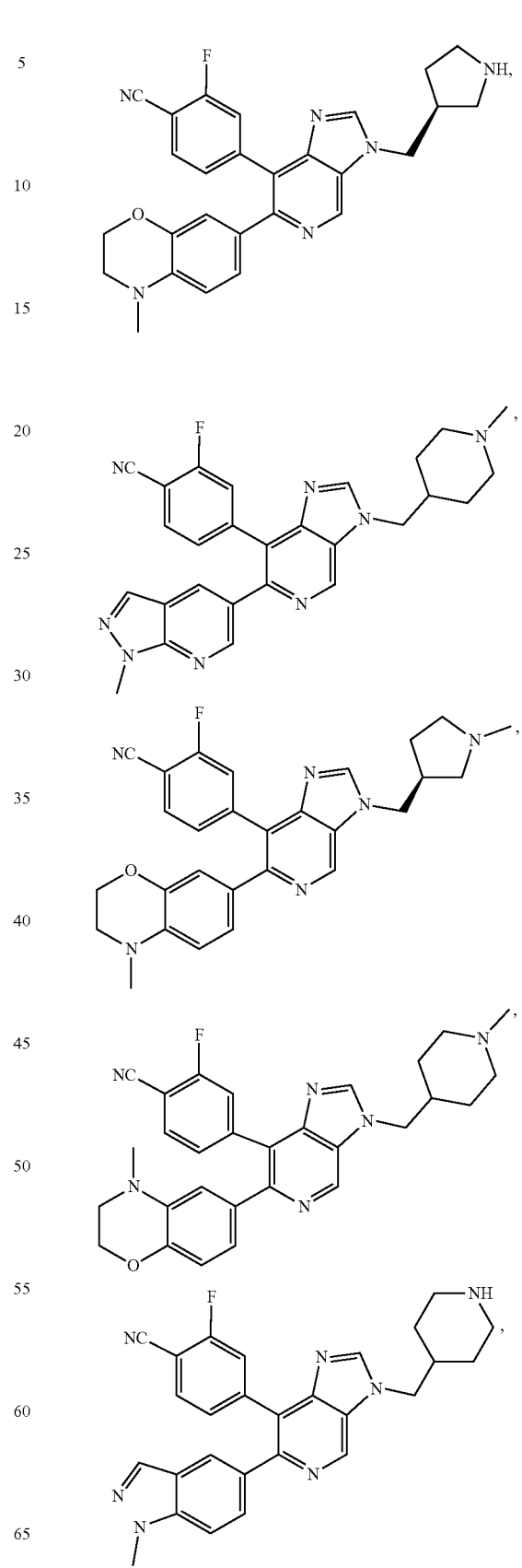

87
-continued
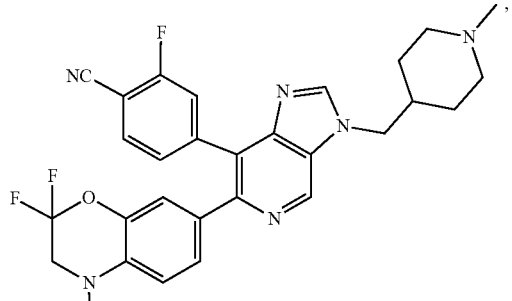
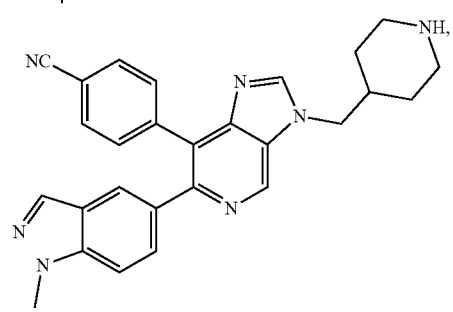
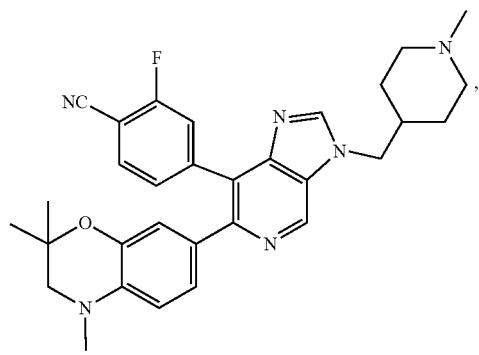
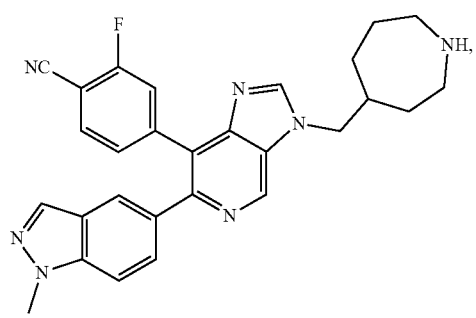
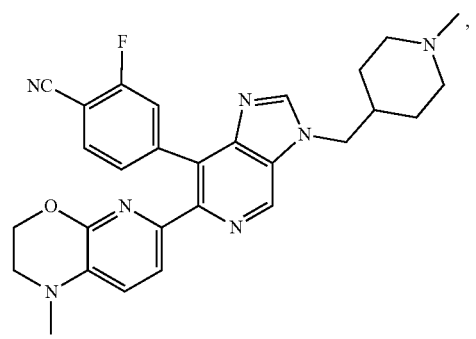
88
-continued
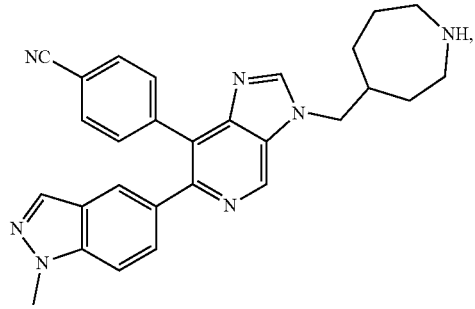
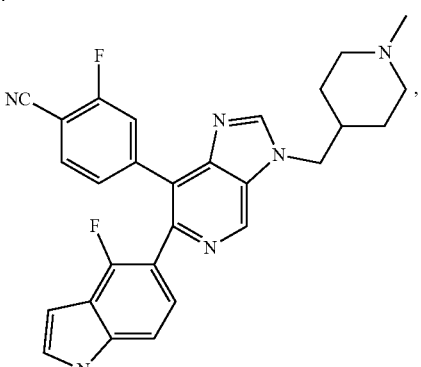
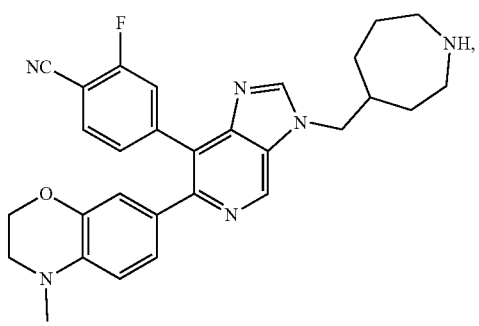
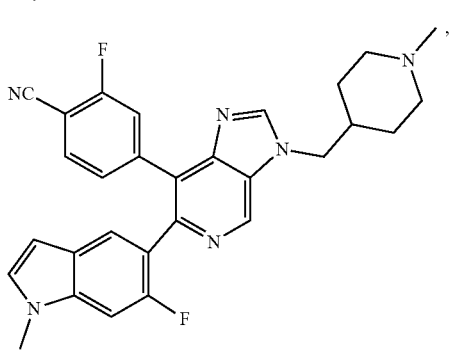
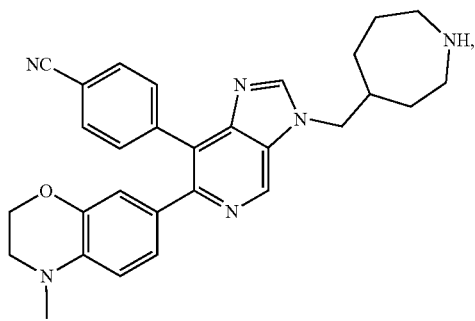

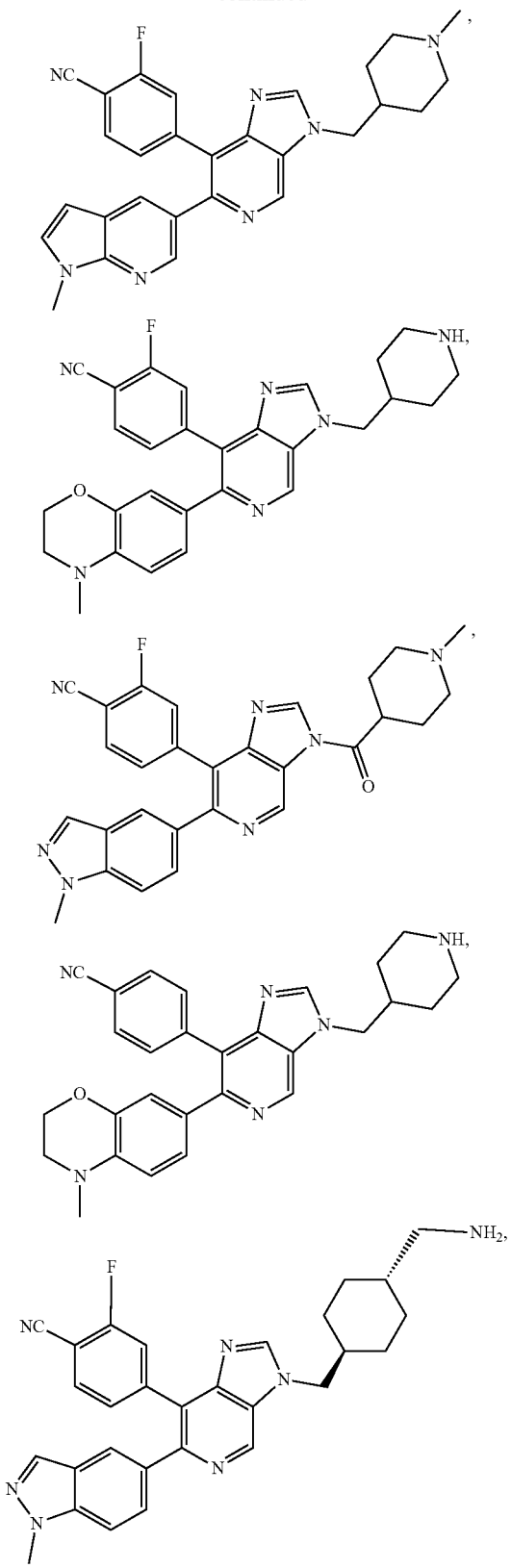

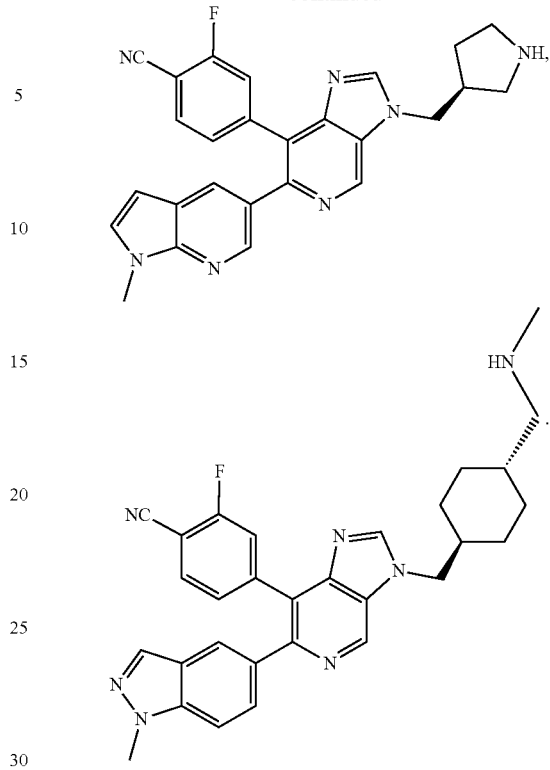

10. A pharmaceutical composition comprising the compound of claim 1, or a pharmaceutically acceptable salt or solvate thereof, and a pharmaceutically acceptable carrier.

11. A method of treating a patient, the method comprising administering to the patient a therapeutically effective amount of the compound of claim 1, or a pharmaceutically acceptable salt or solvate thereof, wherein the patient has a cancer selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt® lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

12. A kit comprising the compound of claim 1, or a pharmaceutically acceptable salt or solvate thereof, and instructions for administering the compound, or a pharmaceutically acceptable salt or solvate thereof, to a patient having a cancer selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitts lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

* * * * *

UNITED STATES PATENT AND TRADEMARK OFFICE
CERTIFICATE OF CORRECTION

PATENT NO. : 11,944,614 B2
APPLICATION NO. : 17/052626
DATED : April 2, 2024
INVENTOR(S) : Shaomeng Wang et al.

Page 1 of 1

It is certified that error appears in the above-identified patent and that said Letters Patent is hereby corrected as shown below:

In the Claims

At Column 76, Lines 5-10, " 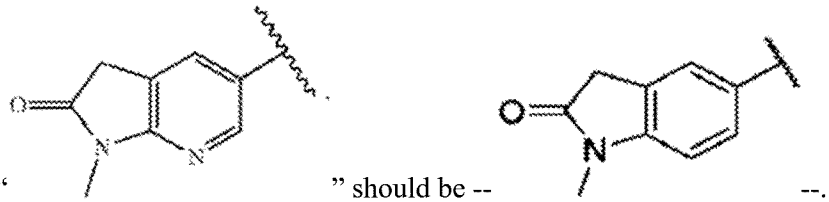 " should be -- --.

At Column 77, Lines 19-20, "(heterocyclo)-$CH^2$—." should be -- (heterocyclo)-$CH_2$—. --.

At Column 90, Line 44, "Burkitt®" should be -- Burkitt's --.

At Column 90, Line 58, "Burkitts" should be -- Burkitt's --.

Signed and Sealed this
Fifth Day of November, 2024

Katherine Kelly Vidal
*Director of the United States Patent and Trademark Office*